United States Patent
Yoshimoto et al.

(10) Patent No.: US 11,905,565 B2
(45) Date of Patent: *Feb. 20, 2024

(54) KIT, DEVICE AND METHOD FOR DETECTING PROSTATE CANCER

(71) Applicants: TORAY INDUSTRIES, INC., Tokyo (JP); NATIONAL CANCER CENTER, Tokyo (JP)

(72) Inventors: Makiko Yoshimoto, Kamakura (JP); Hiroko Sudo, Kamakura (JP); Atsuko Miyano, Kamakura (JP); Satoko Kozono, Kamakura (JP); Takahiro Ochiya, Tokyo (JP); Hiroyuki Fujimoto, Tokyo (JP); Fumihiko Urabe, Tokyo (JP); Juntaro Matsuzaki, Tokyo (JP)

(73) Assignees: TORAY INDUSTRIES, INC., Tokyo (JP); NATIONAL CANCER CENTER, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/988,959

(22) Filed: Nov. 17, 2022

(65) Prior Publication Data

US 2023/0212687 A1 Jul. 6, 2023

Related U.S. Application Data

(62) Division of application No. 17/265,060, filed as application No. PCT/JP2019/031550 on Aug. 9, 2019, now Pat. No. 11,535,899.

(30) Foreign Application Priority Data

Aug. 10, 2018 (JP) ................................ 2018-151952

(51) Int. Cl.
  *C12Q 1/6886* (2018.01)
(52) U.S. Cl.
  CPC ..... *C12Q 1/6886* (2013.01); *C12Q 2600/158* (2013.01); *C12Q 2600/178* (2013.01)
(58) Field of Classification Search
  None
  See application file for complete search history.

(56) References Cited

U.S. PATENT DOCUMENTS

| | | |
|---|---|---|
| 2012/0214697 A1 | 8/2012 | Croce et al. |
| 2015/0337332 A1 | 11/2015 | Ruohoa-Baker et al. |
| 2017/0121779 A1 | 5/2017 | Kondou et al. |
| 2017/0356903 A1 | 12/2017 | Domenyuk et al. |
| 2018/0030440 A1 | 2/2018 | Lee et al. |

FOREIGN PATENT DOCUMENTS

| | | |
|---|---|---|
| EP | 2 341 145 A1 | 7/2011 |
| JP | 2013-535982 A | 9/2013 |
| JP | 2015-39365 A | 3/2015 |
| WO | WO 2009/108860 A2 | 9/2009 |
| WO | WO 2010/054386 A2 | 5/2010 |
| WO | WO 2010/062706 A2 | 6/2010 |
| WO | WO 2011/080315 A1 | 7/2011 |
| WO | WO 2012/027206 A1 | 3/2012 |
| WO | WO 2013/022995 A2 | 2/2013 |
| WO | WO 2014/071205 A1 | 5/2014 |
| WO | WO 2014/071226 A1 | 5/2014 |
| WO | WO 2015/190584 A1 | 12/2015 |

OTHER PUBLICATIONS

American Cancer Society, "Prostate Cancer", 2013, pp. 5, 14-26, 32-54, and 68-70.
Berillo et al., "Binding of intronic miRNAs to the mRNAs of host genes encoding intronic miRNAs and proteins that participate in tumourigenesis." Computers in Biology and Medicine, vol. 43, 2013, pp. 1374-1381.
Cheung et al., "Natural variation in human gene expression assesed in lymphoblastoid cells," Nature Genetics, vol. 33, Mar. 2003, pp. 422-425.
Chinese Office Action and Search Report for Chinese Application No. 201580030849.6, dated Apr. 1, 2019.
Cobb et al., "Sepsis gene expression profiling: Murine splenic compared with hepatic responses determined by using complementary DNA microarrays," Crit. Care Med. (2002), vol. 30, No. 12, p. 2711-2721.
Enard et al., "Intra- and Interspecific Variation in Primate Gene Expression Patterns," Science (2002), vol. 296, pp. 340-343.
Eto et al., "Prospect of microRNA toward laboratory medicine gastrointestinal cancer and microRNA" Clinical Chemistry, vol. 43, 2014, pp. 99-105.
Extended European Search Report for corresponding European Application No. 19847308.4, dated May 9, 2022.
Feng et al., "Combinations of elevated tissue miRNA-17-92 cluster expression and serum prostate-specific antigen as potential diagnostic biomarkers for prostate cancer", Oncology Letters, 2017, vol. 14, pp. 6943-6949.
Gen Bank "*Homo sapiens* microRNA 4443 (MIR4443), MicroRNA," NCBI, Locus: NR_039645, Accession No. NR_039645, Jul. 17, 2013, pp. 1-2.
Gordanpour et al., "MicroRNAs in prostate cancer: from biomarkers to molecularly-based therapeutics," Prostate Cancer and Prostatic Diseases (2012), vol. 15, pp. 314-319.
Hibino et al., "Inhibitors of enhancer of zeste homolog 2 (EZH2) activate tumor-suppressor microRNAs in human cancer cells," Oncogenesis (2014), vol. 3, e104, pp. 1-10.

(Continued)

*Primary Examiner* — Katherine D Salmon
(74) *Attorney, Agent, or Firm* — Birch, Stewart, Kolasch & Birch, LLP

(57) ABSTRACT

This invention provides a kit or device for detection of prostate cancer and a method for detecting prostate cancer. This invention provides a kit or device for detection of prostate cancer comprising a nucleic acid capable of specifically binding to an miRNA in a sample from a subject or a complementary strand thereof and a method for detecting prostate cancer comprising measuring the miRNA in vitro.

6 Claims, 10 Drawing Sheets

Specification includes a Sequence Listing.

(56) References Cited

OTHER PUBLICATIONS

Hoshikawa et al., "Hypoxia induces different genes in the lungs of rats compared with mice," Physiol Genomics, vol. 12, (2002), pp. 209-219.
Huang, et al., "Extracellular MicroRNAs in Urologic Malignancies: Chances and Challenges", International Journal of Molecular Sciences, vol. 14, No. 7, 2013, pp. 14785-14799.
International Search Report for PCT/JP2015/066964 (PCT/ISA/210) dated Sep. 1, 2015.
International Search Report, issued in PCT/JP2019/031550, dated Sep. 10, 2019:.
Japanese Office Action dated Jul. 2, 2019 for Application No. 2016-527882.
Jima et al., "Deep sequencing of the small RNA transcriptome of normal and malignant human B cells identifies hundreds of novel microRNAs," Blood, vol. 116, No. 23, Dec. 2, 2010 (published online Aug. 23, 2010), pp. 118-127 (11 pages total).
Kobayashi et al., "Identification of miR-30d as a novel prognostic maker of prostate cancer," Oncotarget, vol. 3, No. 11, Nov. 2012, pp. 1455-1471.
Kozomara et al., "miRBase: annotating high confidence microRNAs using deep sequencing data", Nucleic Acids Research, vol. 42, 2014, Database issue, pp. D68-D73.
Lee et al., "MicroRNA-Regulated Protein-Protein Interaction Networks and Their Functions in Breast Cancer," Int. J. Mol. Sci., vol. 14, 2013, pp. 11560-11606.
Lieb et al., "Serum levels of miR-320 family members are associated with clinical parameters and diagnosis in prostate cancer patients", Oncotarget, 2018, vol. 9, No. 12, pp. 10402-10416.
Liu et al., "MicroRNA expression profile of gastric cancer stem cells in the MKN-45 cancer cell line," Acta Biochim. Biophys, Sin., vol. 46, No. 2, 2014 (Advance Access Publication Jan. 2, 2014), pp. 92-99.
Mahn, et al., "Circulating microRNAs (miRNA) in Serum of Patients with Prostate Cancer", Urology, vol. 77, No. 5, 2011, pp. 1265. e9-1265.e16.
Mitchell et al., "Circulating microRNAs as stable blood-based markers for cancer detection", PNAS, vol. 105, No. 30, 2008, pp. 10513-10518.
Office Action dated Aug. 23, 2021, in Republic of Korea Patent Application No. 10-2017-7000938.
Office Action dated Jan. 4, 2022, in Japanese Patent Application No. 2020-075338.
Partial European Search Report dated Mar. 4, 2021, in European Patent Application No. 20207829.1.
Partial Supplementary European Search Report for European Application No. 15806052.5, dated Dec. 15, 2017.
Qiagen, "miScript miRNA PCR Array (384-well, 384HC) Human miR Base Profiler HC Plate 4," Sample & Assay Technologies, 2012, 10 pages.
Shen et al., "Exploration of Genome-Wide Circulating MicroRNA in Hepatocellular Carcinoma: MIR-483-5p as a Potential Biomarker," Cancer Epidemiol Biomarkers Prev., vol. 22, No. 12, Dec. 2013, pp. 2364-2373 (11 pages).
Sobin, et al., "TNM Classification of Malignant Tumours", International Union Against Cancer, 7th edition, 2010, pp. 230 to 234.
Takizawa et al., "miRNA Profiling in Serum Samples Using DNA Chip 3D-Gene", BIO Clinica, vol. 29, No. 6, 2014, pp. 588-589.
Technical Document "miScript™ miRNA PCR Array (384-well, 384HC) Human miRBase Profiler HC Plate 5," Document No. 1073798, Aug. 2012, QIAGEN, from https://b2b.qiagen.com/~/media/genetable/mi/hs/34/mihs-3405z.
Toray Industries, Inc., "Kyoto Univ. 3D-Gene Human miRNA Oligo chip v11.0," NCBI, GEO Accession: GPL7766, May 14, 2009, 12 pages.
U.S. Notice of Allowance for U.S. Appl. No. 16/808,095, dated Jun. 16, 2022:.
U.S. Office Action for U.S. Appl. No. 16/808,095, dated Feb. 2, 2022:.
U.S. Office Action for U.S. Appl. No. 16/808,095, dated Oct. 8, 2021.
Urabe et al., "Large-scale Circulating microRNA Profiling for the Liquid Biopsy of Prostate Cancer", Clinical Cancer Research, May 15, 2019, vol. 25, No. 10, pp. 3016-3025.
Walter et al., "Comprehensive microRNA Profiling of Prostate Cancer," Journal of Cancer, vol. 4, No. 5, 2013, pp. 350-357.
Wang et al., Tumor-Associated Circulating MicroRNAs as Biomarkers of Cancer, Molecules, vol. 19, No. 2, 2014, pp. 1912-1938.
Watahiki et al., "Plasma miRNAs as Biomarkers to Identify Patients with Castration-Resistant Metastatic Prostate Cancer," Int. J. Mol. Sci. (2013), vol. 14, pp. 7757-7770.
Wolf et al., "American Cancer Society Guideline for the Early Detection of Prostate Cancer", A Cancer Journal for Clinicians, vol. 60, 2010, pp. 70-98.
Written Opinion of the International Searching Authority for PCT/JP2015/066964 (PCT/ISA/237) dated Sep. 1, 2015.
Written Opinion of the International Searching Authority, issued in PCT/JP2019/03.1550, dated Sep. 10, 2019.
Xu et al., "Down-Regulation of miR-3928 Promoted Osteosarcoma Growth," Cellular Physiology and. Biochemistry, vol. 33, 2014, pp. 1547-1556.

SEQUENCE LISTING

```
Sequence total quantity: 33
SEQ ID NO: 1            moltype = RNA   length = 22
FEATURE                 Location/Qualifiers
source                  1..22
                        mol_type = transcribed RNA
                        organism = Homo sapiens
SEQUENCE: 1
atatacaggg ggagactctc at                                              22

SEQ ID NO: 2            moltype = RNA   length = 22
FEATURE                 Location/Qualifiers
source                  1..22
                        mol_type = transcribed RNA
                        organism = Homo sapiens
SEQUENCE: 2
atatacaggg ggagactctt at                                              22

SEQ ID NO: 3            moltype = RNA   length = 23
```

```
FEATURE                 Location/Qualifiers
source                  1..23
                        mol_type = transcribed RNA
                        organism = Homo sapiens
SEQUENCE: 3
cgggtagaga gggcagtggg agg                                                 23

SEQ ID NO: 4            moltype = RNA  length = 21
FEATURE                 Location/Qualifiers
source                  1..21
                        mol_type = transcribed RNA
                        organism = Homo sapiens
SEQUENCE: 4
agcatgacag aggagaggtg g                                                   21

SEQ ID NO: 5            moltype = RNA  length = 22
FEATURE                 Location/Qualifiers
source                  1..22
                        mol_type = transcribed RNA
                        organism = Homo sapiens
SEQUENCE: 5
actgcagtga aggcacttgt ag                                                  22

SEQ ID NO: 6            moltype = RNA  length = 22
FEATURE                 Location/Qualifiers
source                  1..22
                        mol_type = transcribed RNA
                        organism = Homo sapiens
SEQUENCE: 6
aaaagctggg ttgagagggc aa                                                  22

SEQ ID NO: 7            moltype = RNA  length = 22
FEATURE                 Location/Qualifiers
source                  1..22
                        mol_type = transcribed RNA
                        organism = Homo sapiens
SEQUENCE: 7
ttggggtgga gggccaagga gc                                                  22

SEQ ID NO: 8            moltype = RNA  length = 21
FEATURE                 Location/Qualifiers
source                  1..21
                        mol_type = transcribed RNA
                        organism = Homo sapiens
SEQUENCE: 8
gtgggcgggg gcaggtgtgt g                                                   21

SEQ ID NO: 9            moltype = RNA  length = 86
FEATURE                 Location/Qualifiers
source                  1..86
                        mol_type = transcribed RNA
                        organism = Homo sapiens
SEQUENCE: 9
tttggtactt aaagagagga tacccttttgt atgttcactt gattaatggc gaatatacag        60
ggggagactc tcatttgcgt atcaaa                                              86

SEQ ID NO: 10           moltype = RNA  length = 86
FEATURE                 Location/Qualifiers
source                  1..86
                        mol_type = transcribed RNA
                        organism = Homo sapiens
SEQUENCE: 10
tttggtactt gaagagagga tacccttttgt atgttcactt gattaatggc gaatatacag        60
ggggagactc ttatttgcgt atcaaa                                              86

SEQ ID NO: 11           moltype = RNA  length = 75
FEATURE                 Location/Qualifiers
source                  1..75
                        mol_type = transcribed RNA
                        organism = Homo sapiens
SEQUENCE: 11
ggctgtgccg ggtagagagg gcagtgggag gtaagagctc ttcacccttc accaccttct         60
ccacccagca tggcc                                                          75

SEQ ID NO: 12           moltype = RNA  length = 113
FEATURE                 Location/Qualifiers
source                  1..113
                        mol_type = transcribed RNA
                        organism = Homo sapiens
```

```
SEQUENCE: 12
agcatgacag aggagaggtg gaggtaggcg agagtaatat aatttctcca ggagaacatc    60
tgagagggga agttgctttc ctgccctggc cctttcaccc tcctgagttt ggg          113

SEQ ID NO: 13            moltype = RNA   length = 84
FEATURE                  Location/Qualifiers
source                   1..84
                         mol_type = transcribed RNA
                         organism = Homo sapiens
SEQUENCE: 13
gtcagaataa tgtcaaagtg cttacagtgc aggtagtgat atgtgcatct actgcagtga    60
aggcacttgt agcattatgg tgac                                          84

SEQ ID NO: 14            moltype = RNA   length = 72
FEATURE                  Location/Qualifiers
source                   1..72
                         mol_type = transcribed RNA
                         organism = Homo sapiens
SEQUENCE: 14
ataaattaat ccctctcttt ctagttcttc ctagagtgag gaaaagctgg gttgagaggg    60
caaacaaatt aa                                                       72

SEQ ID NO: 15            moltype = RNA   length = 71
FEATURE                  Location/Qualifiers
source                   1..71
                         mol_type = transcribed RNA
                         organism = Homo sapiens
SEQUENCE: 15
gtctcttagg ctttctcttc ccagatttcc caaagttggg aaaagctggg ttgagagggc    60
aaaaggaaaa a                                                        71

SEQ ID NO: 16            moltype = RNA   length = 61
FEATURE                  Location/Qualifiers
source                   1..61
                         mol_type = transcribed RNA
                         organism = Homo sapiens
SEQUENCE: 16
gagggttggg gtggagggcc aaggagctgg gtggggtgcc aagcctctgt ccccacccca    60
g                                                                   61

SEQ ID NO: 17            moltype = RNA   length = 73
FEATURE                  Location/Qualifiers
source                   1..73
                         mol_type = transcribed RNA
                         organism = Homo sapiens
SEQUENCE: 17
gtgggcgggg gcaggtgtgt ggtgggtggt ggcctgcggt gagcagggcc ctcacacctg    60
cctcgccccc cag                                                      73

SEQ ID NO: 18            moltype = RNA   length = 24
FEATURE                  Location/Qualifiers
source                   1..24
                         mol_type = transcribed RNA
                         organism = Homo sapiens
SEQUENCE: 18
atatacaggg ggagactctc attt                                          24

SEQ ID NO: 19            moltype = RNA   length = 15
FEATURE                  Location/Qualifiers
source                   1..15
                         mol_type = transcribed RNA
                         organism = Homo sapiens
SEQUENCE: 19
atatacaggg ggaga                                                    15

SEQ ID NO: 20            moltype = RNA   length = 23
FEATURE                  Location/Qualifiers
source                   1..23
                         mol_type = transcribed RNA
                         organism = Homo sapiens
SEQUENCE: 20
aatatacagg gggagactct tat                                           23

SEQ ID NO: 21            moltype = RNA   length = 15
FEATURE                  Location/Qualifiers
source                   1..15
                         mol_type = transcribed RNA
                         organism = Homo sapiens
SEQUENCE: 21
```

```
atatacaggg ggaga                                                         15

SEQ ID NO: 22           moltype = RNA   length = 26
FEATURE                 Location/Qualifiers
source                  1..26
                        mol_type = transcribed RNA
                        organism = Homo sapiens
SEQUENCE: 22
cgggtagaga gggcagtggg aggtaa                                             26

SEQ ID NO: 23           moltype = RNA   length = 15
FEATURE                 Location/Qualifiers
source                  1..15
                        mol_type = transcribed RNA
                        organism = Homo sapiens
SEQUENCE: 23
cgggtagaga gggca                                                         15

SEQ ID NO: 24           moltype = RNA   length = 24
FEATURE                 Location/Qualifiers
source                  1..24
                        mol_type = transcribed RNA
                        organism = Homo sapiens
SEQUENCE: 24
aaaagctggg ttgagagggc aaaa                                               24

SEQ ID NO: 25           moltype = RNA   length = 16
FEATURE                 Location/Qualifiers
source                  1..16
                        mol_type = transcribed RNA
                        organism = Homo sapiens
SEQUENCE: 25
aaaagctggg ttgaga                                                        16

SEQ ID NO: 26           moltype = RNA   length = 25
FEATURE                 Location/Qualifiers
source                  1..25
                        mol_type = transcribed RNA
                        organism = Homo sapiens
SEQUENCE: 26
actgcagtga aggcacttgt agcat                                              25

SEQ ID NO: 27           moltype = RNA   length = 16
FEATURE                 Location/Qualifiers
source                  1..16
                        mol_type = transcribed RNA
                        organism = Homo sapiens
SEQUENCE: 27
actgcagtga aggcac                                                        16

SEQ ID NO: 28           moltype = RNA   length = 24
FEATURE                 Location/Qualifiers
source                  1..24
                        mol_type = transcribed RNA
                        organism = Homo sapiens
SEQUENCE: 28
aaaagctggg ttgagagggc aaaa                                               24

SEQ ID NO: 29           moltype = RNA   length = 16
FEATURE                 Location/Qualifiers
source                  1..16
                        mol_type = transcribed RNA
                        organism = Homo sapiens
SEQUENCE: 29
aaaagctggg ttgaga                                                        16

SEQ ID NO: 30           moltype = RNA   length = 23
FEATURE                 Location/Qualifiers
source                  1..23
                        mol_type = transcribed RNA
                        organism = Homo sapiens
SEQUENCE: 30
ttggggtgga gggccaagga gct                                                23

SEQ ID NO: 31           moltype = RNA   length = 16
FEATURE                 Location/Qualifiers
source                  1..16
                        mol_type = transcribed RNA
                        organism = Homo sapiens
```

```
SEQUENCE: 31
ttggggtgga gggcca                                                              16

SEQ ID NO: 32           moltype = RNA  length = 22
FEATURE                 Location/Qualifiers
source                  1..22
                        mol_type = transcribed RNA
                        organism = Homo sapiens
SEQUENCE: 32
gtgggcgggg gcaggtgtgt gg                                                       22

SEQ ID NO: 33           moltype = RNA  length = 15
FEATURE                 Location/Qualifiers
source                  1..15
                        mol_type = transcribed RNA
                        organism = Homo sapiens
SEQUENCE: 33
cgggggcagg tgtgt                                                               15
```

KIT, DEVICE AND METHOD FOR DETECTING PROSTATE CANCER

CROSS-REFERENCE TO RELATED APPLICATIONS

This application is a Divisional of U.S. application Ser. No. 17/265,060 filed Feb. 1, 2021, which is the National Phase of PCT International Application No. PCT/JP2019/031550, filed on Aug. 9, 2019, which claims priority under 35 U.S.C. § 119(a) to Patent Application No. 2018-151952, filed in Japan on Aug. 10, 2018, all of which are hereby expressly incorporated by reference into the present application.

REFERENCE TO ELECTRONIC SEQUENCE LISTING

The application contains a Sequence Listing which has been submitted electronically in .XML format and is hereby incorporated by reference in its entirety. Said .XML copy, created on Nov. 1, 2022, is named "PH-8028-PCT-US-DIV" and is 30,443 bytes in size. The sequence listing contained in this .XML file is part of the specification and is hereby incorporated by reference herein in its entirety.

TECHNICAL FIELD

The present invention relates to a kit or device for detection of prostate cancer comprising a nucleic acid capable of specifically binding to a specific miRNA or a complementary strand thereof, which is used for examining the presence or absence of prostate cancer in a subject, and a method for detecting prostate cancer comprising measuring the expression level of the miRNA.

BACKGROUND ART

The prostate is an organ that produces a part of seminal fluid and is located below the bladder and in front of the rectum. Prostate cancer is a disease developed by repetition of disorganized growth of prostate cells. According to the statistics on cancer depending on sites in Japan (2013) disclosed by National Cancer Center Japan, Center for Cancer Control and Information Service, the number of prostate cancer patients was 74,861. That is, it is deduced that 1 out of 11 Japanese men would have prostate cancer, and prostate cancer is the fourth most commonly occurring cancer in men. The number of people died of prostate cancer is as many as 11,803, and the mortality rate thereof ranks seventh in men. According to American Cancer Society, in U.S.A., it is deduced that 1 out of 7 men develops prostate cancer. In particular, elderly people often develop prostate cancer, and 6 out of 10 men aged 65 years or older are diagnosed to have prostate cancer. The putative number of prostate cancer patients was as many as 233,000 in 2014 in U.S.A., and approximately 29,480 patients among them are assumed to die.

It is said that prostate cancer is developed from some benign diseases, such as prostatic hyperplasia or prostatitis, which are premalignant lesions of prostate cancer. The stage of prostate cancer progression is defined in "TNM Classification of Malignant Tumors, Vol. 7" (Sobin, L. et al., 2010, pp. 230 to 234) and is classified into stage I (T1 to T2a/N0/M0), stage II (T2b to c/N0/M0), stage III (T3/N0/M0), or stage IV (T4/N0/M0, N1, and cM1) depending on tumor spread patterns (T1a to c, T2a to c, T3a to b, T4), metastatic patterns, such as no lymph node metastasis (N0), with lymph node metastasis (N1), no distant metastasis (M0), or with distant metastasis (M1), and other conditions.

In addition, the Gleason grading system is defined as the indicator for the degree of prostate cancer malignancy. According to the American Cancer Society, the Gleason Scores evaluate the degree of malignancy of prostate cancer tissue lesions on a 1-5 scale, and the sum of the lesion with the largest quantity of prostate cancer tissue and the lesion with the second-largest quantity of prostate cancer tissue; 2 to 10, is designated as the Gleason score. A Gleason score of 6 or less is considered to be low malignancy, a Gleason score of 7 is considered to be moderate malignancy, and a Gleason score of 8 or more is considered to be high malignancy.

Since prostate cancer progression is relatively slow in many cases, a relative 5-year survival rate is almost 100%. That is, prostate cancer is one of cancers with the most optimistic prognosis. However, prostate cancer progression is relatively fast, various types of disorders or symptoms may appear in some cases, and a relative 5-year survival rate of stage IV prostate cancer with distant metastasis is as low as 28%.

In prostate cancer diagnosis, the PSA test is extensively employed as a primary test comprising assaying the blood tumor marker (PSA). When a high PSA level is detected, rectal examination or transrectal ultrasonography of the prostate is performed. When prostate cancer is further suspected, the diagnosis is confirmed through biopsy. When distant metastasis is suspected, imaging tests, such as CT, MRI, and bone scintigraphy, are also performed.

The prostate-specific antigen (PSA) is generated in the prostate gland, it is contained in seminal fluid, and a very small amount of PSA is also present in blood. In general, the normal blood PSA level of healthy male subjects is considered to be 4 ng/ml or lower. When the PSA level exceeds the standard value, prostate cancer is suspected. Since the blood PSA level elevates in case of early asymptomatic prostate cancer and it is associated with cancer progression, the blood PSA level is considered useful and widely used. In addition, the American Cancer Society recommends early detection of prostate cancer and the PSA test for subjects who want to screening for prostate cancer.

In principle, available prostate cancer treatment techniques include surgical treatment, radiation treatment, endocrine treatment (hormonal treatment), and watchful waiting by which observation is continued while monitoring a tumor marker (PSA) without performing special treatment. In particular, there are several options for treatment of early prostate cancer, in addition to watchful waiting, such as external radiation treatment, internal radiation treatment (brachytherapy), radical prostatectomy, and cryosurgery.

As described above, the PSA test has been extensively employed for tumor marker testing of prostate cancer; however, the PSA test is known to evaluate 15% of male patients exhibiting PSA of 4 ng/ml or lower, which is the standard blood level, as having prostate cancer via biopsy. Since blood PSA levels are elevated in male patients with benign (non-cancerous) prostatic hyperplasia and prostatitis and healthy elderly men, the PSA test is known to provide false-positive results. In addition, erroneous detection of cancers other than prostate cancer would lead to false-positive results. Such high false-positive results provided by the PSA test would lead to overdiagnosis and overtreatment, and various secondary diseases resulting from unnecessary treatment of prostate cancer have been an issue of concern in recent years. According to large-scale study conducted by recruiting 5,000 or more subjects (Wolf, A M. et al., 2010, A Cancer Journal for Clinicians, Vol. 60 (2), pp. 70-98), the PSA test performance is low. Specifically, sensitivity is as low as 20.5% in the entire prostate cancer cases, sensitivity is as low as 51% in prostate cancer cases with high malignancy, and significance of a tumor marker assay as a preoperative test is considered to be low.

Patent Literatures 1 and 2 and Non-Patent Literatures 1 and 2 each report detection of prostate cancer based on the microRNA (miRNA) expression level in a biological sample including blood or the miRNA expression level in combination with the expression level of other markers, although such techniques are still in the research phase.

Patent Literature 1 discloses a method for detection of prostate cancer using miR-1275 in the blood derived from prostate cancer; however, reliability of this method is low due to an extremely small number of target cases, which is 2 to 9.

Patent Literature 2 discloses a method for distinguishing a prostate cancer patient from a healthy subject or a breast cancer patient with the use of 1 to 4 types of miRNAs in combination selected from among miR-6819-5p, miR-1228-5p, and the like in the blood. While one of the most important objectives of prostate cancer diagnosis is to distinguish prostate cancer from benign prostatic diseases, it is not possible to achieve such expected objective by the method disclosed in Patent Literature 2, and clinical utility value of such technique is not sufficient.

Non-Patent Literature 1 describes that the miR-320a/-b/-c expression levels in the serum are useful to distinguish prostate cancer patients from healthy subjects or prostatic hyperplasia patients. In Non-Patent Literature 1, the miR-320a/-b/-c expression levels in prostatic hyperplasia patients are significantly higher than those in healthy subjects, such expression levels in prostate cancer patients are significantly lower than those in prostatic hyperplasia patients, and such expression levels in prostate cancer patients are significantly higher than those in healthy subjects. That is, the correlation: healthy subjects <prostate cancer <prostatic hyperplasia, is established. If a discriminant threshold is designated between, for example, healthy subjects and prostate cancer patients in such correlation, prostatic hyperplasia patients are erroneously evaluated as cancer patients, which indicates that members of the positive group may have prostate cancer or prostatic hyperplasia, and it is impossible to determine whether or not a subject has cancer. Since prostatic hyperplasia is a premalignant lesion of prostate cancer, in principle, it is necessary that the miR-320a/-b/-c expression levels are increased in ascending order; healthy subjects <prostatic hyperplasia patients <prostate cancer patients (or in descending order: healthy subjects >prostatic hyperplasia patients >prostate cancer patients). In Non-Patent Literature 1, the negative group made of healthy subjects and prostatic hyperplasia patients cannot be distinguished from the positive group made of prostate cancer patients, as needed in clinical settings. Thus, the method of Non-Patent Literature 1 is not practical.

Non-Patent Literature 2 demonstrates that the miR-17-92 cluster including miR-17-3p in the tissue samples obtained at the time of surgery is useful to distinguish prostate cancer from prostatic hyperplasia. However, prostate cancer can be distinguished from benign prostatic diseases including hyperplasia via surgery. In other words, clinical utility of such technique is effective only when prostate cancer can be distinguished from benign prostatic diseases prior to surgery. If the presence or absence of prostate cancer is found after surgery as described in Non-Patent Literature 2, the industrial value thereof is very low.

CITATION LIST

Patent Literature

Patent Literature 1: JP Patent Publication (Kokai) No. 2015-039365 A
Patent Literature 2: WO 2015/190584

Non-Patent Literature

Non-Patent Literature 1: Lieb, B. et al., 2018, Oncotarget, Vol. 9 (12), pp. 10402-10416
Non-Patent Literature 2: Feng, S. et al., 2017, Oncology Letters, Vol. 14 (6), pp. 6943-6949

SUMMARY OF INVENTION

Problems to be Solved by the Invention

As described above, several reports have been made concerning evaluation of prostate cancer using the microRNA (miRNA) expression levels in biological samples including blood samples, although such techniques are still in the study phase and none of such techniques is not yet in practical use. The invention of Patent Literature 1 was actually examined. As described in Comparative Example 1 below, as a result, no difference was observed in the miR-1275 expression levels between the samples obtained from prostate cancer patients and the samples obtained from benign prostatic disease patients. When the expression level of 7.8 is used as the threshold, for example, sensitivity is 55%, and specificity is 47%. That is, such performance is not sufficient to distinguish prostate cancer from benign diseases, and such technique cannot be employed for clinical testing.

Accordingly, the present invention is intended to discover a novel tumor marker for prostate cancer with high reliability and utility that can distinguish prostate cancer from benign prostatic diseases including hyperplasia required in clinical settings and to provide a disease diagnosis kit or device that is useful for non-invasive diagnosis and treatment of prostate cancer with a small amount of samples and a method for determining (or detecting) prostate cancer with the use of a nucleic acid that can specifically bind to such marker.

Means for Solution to Problem

The present inventors have conducted concentrated studies in order to dissolve the problems described above. As a result, they have discovered genes available as prostate cancer detection markers from blood, which can be collected in a low-invasive manner, and they have discovered that prostate cancer can be detected significantly with the use of such genes. This has led to the completion of the present invention.

<Summary of Invention>

Specifically, the present invention includes the following aspects.

(1) A kit for detection of prostate cancer comprising a nucleic acid capable of specifically binding to at least one polynucleotide selected from the following prostate cancer markers; miR-1185-2-3p, miR-1185-1-3p, miR-197-5p, and miR-6076, or a polynucleotide consisting of a nucleotide sequence complementary to the polynucleotide.

(2) The kit according to (1), wherein the nucleic acid is a polynucleotide selected from the group consisting of the following polynucleotides (a) to (e):
  (a) a polynucleotide consisting of a nucleotide sequence shown in any of SEQ ID NOs: 1 to 4 or a nucleotide sequence derived therefrom by the replacement of u with t, a variant thereof, a derivative thereof, or a fragment thereof comprising 15 or more consecutive nucleotides;
  (b) a polynucleotide comprising a nucleotide sequence shown in any of SEQ ID NOs: 1 to 4;
  (c) a polynucleotide consisting of a nucleotide sequence complementary to a nucleotide sequence shown in any of SEQ ID NOs: 1 to 4 or a nucleotide sequence derived therefrom by the replacement of u with t, a variant thereof, a derivative thereof, or a fragment thereof comprising 15 or more consecutive nucleotides;
  (d) a polynucleotide comprising a nucleotide sequence complementary to a nucleotide sequence shown in any of SEQ ID NOs: 1 to 4 or a nucleotide sequence derived therefrom by the replacement of u with t; and
  (e) a polynucleotide hybridizing under stringent conditions to any of the polynucleotides (a) to (d).

(3) The kit according to (1) or (2), which further comprises a nucleic acid capable of specifically binding to at least one polynucleotide selected from the following other prostate cancer markers: miR-17-3p, miR-320b, miR-6819-5p, and miR-1228-5p, or a polynucleotide consisting of a nucleotide sequence complementary to the polynucleotide.

(4) The kit according to (3), wherein the nucleic acid is a polynucleotide selected from the group consisting of the following polynucleotides (f) to (j):
  (f) a polynucleotide consisting of a nucleotide sequence shown in any of SEQ ID NOs: 5 to 8 or a nucleotide sequence derived therefrom by the replacement of u with t, a variant thereof, a derivative thereof, or a fragment thereof comprising 15 or more consecutive nucleotides;
  (g) a polynucleotide comprising a nucleotide sequence shown in any of SEQ ID NOs: 5 to 8;
  (h) a polynucleotide consisting of a nucleotide sequence complementary to a nucleotide sequence shown in any of SEQ ID NOs: 5 to 8 or a nucleotide sequence derived therefrom by the replacement of u with t, a variant thereof, a derivative thereof, or a fragment thereof comprising 15 or more consecutive nucleotides;
  (i) a polynucleotide comprising a nucleotide sequence complementary to a nucleotide sequence shown in any of SEQ ID NOs: 5 to 8 or a nucleotide sequence derived therefrom by the replacement of u with t; and
  (j) a polynucleotide hybridizing under stringent conditions to any of the polynucleotides (f) to (i).

(5) A device for detection of prostate cancer comprising a nucleic acid capable of specifically binding to at least one polynucleotide selected from the following prostate cancer markers: miR-1185-2-3p, miR-1185-1-3p, miR-197-5p, and miR-6076, or a polynucleotide consisting of a nucleotide sequence complementary to the polynucleotide.

(6) The device according to (5), wherein the nucleic acid is a polynucleotide selected from the group consisting of the following polynucleotides (a) to (e):
  (a) a polynucleotide consisting of a nucleotide sequence shown in any of SEQ ID NOs: 1 to 4 or a nucleotide sequence derived therefrom by the replacement of u with t, a variant thereof, a derivative thereof, or a fragment thereof comprising 15 or more consecutive nucleotides;
  (b) a polynucleotide comprising a nucleotide sequence shown in any of SEQ ID NOs: 1 to 4;
  (c) a polynucleotide consisting of a nucleotide sequence complementary to a nucleotide sequence shown in any of SEQ ID NOs: 1 to 4 or a nucleotide sequence derived therefrom by the replacement of u with t, a variant thereof, a derivative thereof, or a fragment thereof comprising 15 or more consecutive nucleotides;
  (d) a polynucleotide comprising a nucleotide sequence complementary to a nucleotide sequence shown in any of SEQ ID NOs: 1 to 4 or a nucleotide sequence derived therefrom by the replacement of u with t; and
  (e) a polynucleotide hybridizing under stringent conditions to any of the polynucleotides (a) to (d).

(7) The device according to (5) or (6), which further comprises a nucleic acid capable of specifically binding to at least one polynucleotide selected from the following other prostate cancer markers: miR-17-3p, miR-320b, miR-6819-5p, and miR-1228-5p, or a polynucleotide consisting of a nucleotide sequence complementary to the polynucleotide.

(8) The device according to (7), wherein the nucleic acid is a polynucleotide selected from the group consisting of the following polynucleotides (f) to (j):
  (f) a polynucleotide consisting of a nucleotide sequence shown in any of SEQ ID NOs: 5 to 8 or a nucleotide sequence derived therefrom by the replacement of u with t, a variant thereof, a derivative thereof, or a fragment thereof comprising 15 or more consecutive nucleotides;
  (g) a polynucleotide comprising a nucleotide sequence shown in any of SEQ ID NOs: 5 to 8;
  (h) a polynucleotide consisting of a nucleotide sequence complementary to a nucleotide sequence shown in any of SEQ ID NOs: 5 to 8 or a nucleotide sequence derived therefrom by the replacement of u with t, a variant thereof, a derivative thereof, or a fragment thereof comprising 15 or more consecutive nucleotides;
  (i) a polynucleotide comprising a nucleotide sequence complementary to a nucleotide sequence shown in any of SEQ II) NOs: 5 to 8 or a nucleotide sequence derived therefrom by the replacement of u with t; and
  (j) a polynucleotide hybridizing under stringent conditions to any of the polynucleotides (f) to (i).

(9) The device according to any of (5) to (8), which is used for measurement by a hybridization technique.

(10) The device according to (9), wherein the hybridization technique is a nucleic acid array technique.

(11) A method for detecting prostate cancer comprising: measuring an expression level of at least one polynucleotide selected from the following prostate cancer markers: miR-1185-2-3p, miR-1185-1-3p, miR-197-5p, and miR-6076, in a sample from a subject; and evaluating in vitro whether or not the subject has prostate cancer using the measured expression level.

(12) The method according to (11) comprising: plugging the gene expression level of the one or more polynucleotide in the sample from the subject into a discriminant formula capable of discriminating the presence or absence of prostate cancer distinctively, wherein the discriminant formula is created using gene expression levels in samples from subjects known to have prostate cancer and gene expression levels in samples from subjects having no prostate cancer as training samples; and thereby evaluating as to the presence or absence of prostate cancer in vitro.

(13) The method according to (11) or (12) comprising measuring an expression level of the polynucleotide using a nucleic acid capable of specifically binding to the polynucleotide or to a polynucleotide consisting of a nucleotide sequence complementary to the polynucleotide, wherein the nucleic acid is a polynucleotide selected from the group consisting of the following polynucleotides (a) to (e):

(a) a polynucleotide consisting of a nucleotide sequence shown in any of SEQ ID NOs: 1 to 4 or a nucleotide sequence derived therefrom by the replacement of u with t, a variant thereof, a derivative thereof, or a fragment thereof comprising 15 or more consecutive nucleotides;

(b) a polynucleotide comprising a nucleotide sequence shown in any of SEQ ID NOs: 1 to 4;

(c) a polynucleotide consisting of a nucleotide sequence complementary to a nucleotide sequence shown in any of SEQ ID NOs: 1 to 4 or a nucleotide sequence derived therefrom by the replacement of u with t, a variant thereof, a derivative thereof, or a fragment thereof comprising 15 or more consecutive nucleotides;

(d) a polynucleotide comprising a nucleotide sequence complementary to a nucleotide sequence shown in any of SEQ ID NOs: 1 to 4 or a nucleotide sequence derived therefrom by the replacement of u with t; and (e) a polynucleotide hybridizing under stringent conditions to any of the polynucleotides (a) to (d).

(14) The method according to any of (11) to (13) further comprising measuring an expression level of at least one polynucleotide selected from the following other prostate cancer markers: miR-17-3p, miR-320b, miR-6819-5p, and miR-1228-5p.

(15) The method according to (14) comprising: measuring an expression level of the polynucleotide using a nucleic acid capable of specifically binding to the polynucleotide or to a polynucleotide consisting of a nucleotide sequence complementary to the polynucleotide, wherein the nucleic acid is a polynucleotide selected from the group consisting of the following polynucleotides (f) to (j):

(f) a polynucleotide consisting of a nucleotide sequence shown in any of SEQ ID NOs: 5 to 8 or a nucleotide sequence derived therefrom by the replacement of u with t, a variant thereof, a derivative thereof, or a fragment thereof comprising 15 or more consecutive nucleotides;

(g) a polynucleotide comprising a nucleotide sequence shown in any of SEQ ID NOs: 5 to 8;

(h) a polynucleotide consisting of a nucleotide sequence complementary to a nucleotide sequence shown in any of SEQ ID NOs: 5 to 8 or a nucleotide sequence derived therefrom by the replacement of u with t, a variant thereof, a derivative thereof, or a fragment thereof comprising 15 or more consecutive nucleotides;

(i) a polynucleotide comprising a nucleotide sequence complementary to a nucleotide sequence shown in any of SEQ II) NOs: 5 to 8 or a nucleotide sequence derived therefrom by the replacement of u with t; and (j) a polynucleotide hybridizing under stringent conditions to any of the polynucleotides (f) to (i).

(16) The method according to any of (11) to (15) comprising: measuring an expression level of a target gene in the sample from the subject using the kit according to any of (1) to (4) or the device according to any of (5) to (10), wherein the kit or the device comprises a nucleic acid capable of specifically binding to the polynucleotide or to a polynucleotide consisting of a nucleotide sequence complementary to the polynucleotide.

(17) The method according to any of (11) to (16), wherein the subject is a human.

(18) The method according to any of (11) to (17), wherein the sample is blood, serum, or plasma.

(19) A prostate cancer detection marker comprising at least one polynucleotide selected from the group consisting of miR-1185-2-3p, miR-1185-1-3p, miR-197-5p, and miR-6076.

(20) The marker according to (19), wherein the polynucleotide is at least one polynucleotide selected from the group consisting of the following polynucleotides (a) and (b):

(a) a polynucleotide consisting of a nucleotide sequence shown in any of SEQ ID NOs: 1 to 4; and (b) a polynucleotide comprising a nucleotide sequence shown in any of SEQ ID NOs: 1 to 4.

(21) The prostate cancer detection marker according to (19) or (20), which further comprises at least one polynucleotide selected from the group consisting of miR-17-3p, miR-320b, miR-6819-5p, and miR-1228-5p.

(22) The marker according to (21), wherein the polynucleotide is at least one polynucleotide selected from the group consisting of the following polynucleotides (f) and (g):

(f) a polynucleotide consisting of a nucleotide sequence shown in any of SEQ ID NOs: 5 to 8; and (g) a polynucleotide comprising a nucleotide sequence shown in any of SEQ ID NOs: 5 to 8.

<Definition of Terms>

The terms used herein are defined as described below.

Abbreviations or terms such as nucleotide, polynucleotide, DNA, and RNA abide by "Guidelines for the preparation of specification which contain nucleotide and/or amino acid sequences" (edited by Japan Patent Office) and common use in the art.

The term "polynucleotide" used herein refers to a nucleic acid including any of RNA, DNA, and RNA/DNA (chimera). The DNA includes any of cDNA, genomic DNA, and synthetic DNA. The RNA includes any of total RNA, mRNA, rRNA, miRNA, siRNA, snoRNA, snRNA, non-coding RNA, and synthetic RNA. Here, the "synthetic DNA" and the "synthetic RNA" refer to a DNA and an RNA artificially prepared using, for example, an automatic nucleic acid synthesizer, on the basis of predetermined nucleotide sequences (which may be either a natural or non-natural sequence). The "non-natural sequence" is intended to be used in a broad sense and includes, for example, a sequence comprising substitution, deletion, insertion, and/or addition of one or more nucleotides (i.e., a variant sequence) and a sequence comprising one or more modified nucleotides (i.e., a modified sequence), which are different from the natural sequence. Herein, the term "polynucleotide" is used interchangeably with the term "nucleic acid."

The term "fragment" used herein is a polynucleotide having a nucleotide sequence that consists of a consecutive portion of a polynucleotide and desirably has a length of 15 or more nucleotides, preferably 17 or more nucleotides, and more preferably 19 or more nucleotides.

The term "gene" used herein is intended to include not only RNA and double-stranded DNA but also each single-stranded DNA such as a plus(+) strand (or a sense strand) or a complementary strand (or an antisense strand) constituting the duplex. The gene is not particularly limited by its length.

Thus, the "gene" used herein includes any of double-stranded DNA including human genomic DNA, single-stranded DNA (plus strand), single-stranded DNA having a sequence complementary to the plus strand (complementary strand), cDNA, microRNA (miRNA), their fragments, and human genome, and their transcripts, unless otherwise specified. The "gene" includes not only a "gene" shown in a particular nucleotide sequence (or SEQ ID NO) but also "nucleic acids" encoding RNAs having biological functions equivalent to RNA encoded by the gene, for example, a congener (i.e., a homolog or an ortholog), a variant (e.g., a genetic polymorph), and a derivative. Specific examples of such a "nucleic acid" encoding a congener, a variant, or a derivative can include a "nucleic acid" having a nucleotide sequence hybridizing under stringent conditions described below to a complementary sequence of a nucleotide sequence shown in any of SEQ ID NOs: 1 to 33 or a nucleotide sequence derived therefrom by the replacement of u with t. Regardless of whether or not there is a difference in functional region, the "gene" can comprise, for example, expression control regions, coding regions, exons, or introns. The "gene" may be contained in a cell or may exist alone after being released from a cell. Alternatively, the "gene" may be in a state enclosed in a vesicle referred to as an exosome.

The term "exosome" used herein is a vesicle that is encapsulated by the lipid bilayer and secreted from a cell. The exosome is derived from a multivesicular endosome and may incorporate biomaterials such as "genes" (e.g., RNA or DNA) or proteins when released to an extracellular environment. The exosome is known to be contained in a body fluid such as blood, serum, plasma, or lymph.

The term "transcript" used herein refers to an RNA synthesized from the DNA sequence of a gene as a template. RNA polymerase binds to a site referred to as a promoter located upstream of the gene and adds ribonucleotides complementary to the nucleotide sequence of the DNA to the 3' end to synthesize an RNA. This RNA contains not only the gene itself but also the whole sequence from a transcription initiation site to the end of a poly A sequence, including expression control regions, coding regions, exons, or introns.

Unless otherwise specified, the term "microRNA (miRNA)" used herein is intended to mean a 15- to 25-nucleotide non-coding RNA that is transcribed as an RNA precursor having a hairpin-like structure, cleaved by a dsRNA-cleaving enzyme having RNase III cleavage activity, integrated into a protein complex referred to as RISC, and involved in suppression of mRNA translation. The term "miRNA" used herein includes not only a "miRNA" shown in a particular nucleotide sequence (or SEQ ID NO) but also a "miRNA" comprising a precursor of the "miRNA" (pre-miRNA or pri-miRNA) and having biological functions equivalent to miRNAs encoded thereby, such as a "miRNA" encoding a congener (i.e., a homolog or an ortholog), a variant such as a genetic polymorph, and a derivative. Such a "miRNA" encoding a precursor, a congener, a variant, or a derivative can be specifically identified using "miRBase release 21" (http://www.mirbase.org/), and examples thereof can include a "miRNA" having a nucleotide sequence hybridizing under stringent conditions described below to a complementary sequence of any particular nucleotide sequence shown in any of SEQ ID NOs: 1 to 33. The term "miRNA" used herein may be a gene product of a miR gene. Such a gene product includes a mature miRNA (e.g., a 15- to 25-nucleotide or 19- to 25-nucleotide non-coding RNA involved in suppression of mRNA translation as described above) or a miRNA precursor (e.g., pre-miRNA or pri-miRNA as described above).

The term "probe" used herein includes a polynucleotide that is used for specifically detecting an RNA resulting from the expression of a gene or a polynucleotide derived from the RNA, and/or a polynucleotide complementary thereto.

The term "primer" used herein includes consecutive polynucleotides that specifically recognize and amplify an RNA resulting from the expression of a gene or a polynucleotide derived from the RNA, and/or a polynucleotide complementary thereto.

In this context, the "complementary polynucleotide" (complementary strand or reverse strand) means a polynucleotide in a complementary relationship based on A:T (U) and G:C base pairs with the full-length sequence of a polynucleotide consisting of a nucleotide sequence defined by any of SEQ ID NOs: 1 to 33 or a nucleotide sequence derived therefrom by the replacement of u with t, or a partial sequence thereof (here, this full-length or partial sequence is referred to as a plus strand for the sake of convenience). However, such a complementary strand is not limited to a sequence completely complementary to the nucleotide sequence of the target plus strand and may have a complementary relationship to an extent that permits hybridization under stringent conditions to the target plus strand.

The term "stringent conditions" used herein refers to conditions under which a nucleic acid probe hybridizes to its target sequence to a detectably larger extent (e.g., a measurement value equal to or larger than "(a mean of background measurement values)+(a standard deviation of the background measurement values)×2") than that for other sequences. The stringent conditions are dependent on a sequence and differ depending on an environment where hybridization is performed. A target sequence complementary 100% to the nucleic acid probe can be identified by controlling the stringency of hybridization and/or washing conditions. Specific examples of the "stringent conditions" will be mentioned below.

The term "Tm value" used herein means a temperature at which the double-stranded moiety of a polynucleotide is denatured into single strands so that the double strands and the single strands exist at a ratio of 1:1.

The term "variant" used herein means, in the case of a nucleic acid, a natural variant attributed to polymorphism, mutation, or the like; a variant comprising deletion, substitution, addition, or insertion of 1, 2, 3, or more (e.g., 1 to several) nucleotides in a nucleotide sequence shown in any of SEQ ID NOs: 1 to 8, a nucleotide sequence derived therefrom by the replacement of u with t, or a partial sequence thereof; a variant comprising deletion, substitution, addition, or insertion of 1, 2, or more nucleotides in a nucleotide sequence of a precursor RNA (a premature miRNA) of the sequence of any of SEQ ID NOs: 1 to 8, a nucleotide sequence derived therefrom by the replacement of u with t, or a partial sequence thereof; a variant exhibiting percent (%) identity of approximately 90% or higher, approximately 95% or higher, approximately 97% or higher, approximately 98% or higher, or approximately 99% or higher to each of these nucleotide sequences or the partial sequences thereof; or a nucleic acid hybridizing under the stringent conditions defined above to a polynucleotide or an oligonucleotide comprising each of these nucleotide sequences or the partial sequences thereof.

The term "several" used herein means an integer of approximately 10, 9, 8, 7, 6, 5, 4, 3, or 2.

The variant as used herein can be prepared by a well-known technique such as site-directed mutagenesis or mutagenesis using PCR.

The term "percent (%) identity" used herein can be determined with or without an introduced gap, using a protein or gene search system based on BLAST (https://blast.ncbi.nlm.nih.gov/Blast.cgi) or FASTA (http://www.genome.jp/tools/fasta/) (Zheng Zhang et al., 2000, J. Comput. Biol., Vol. 7, pp. 203-214; Altschul, S. F. et al., 1990, Journal of Molecular Biology, Vol. 215, pp. 403-410; and Pearson, W. R. et al., 1988, Proc. Natl. Acad. Sci. U.S.A., Vol. 85, pp. 2444-2448).

The term "derivative" used herein is meant to include unlimitedly a modified nucleic acid, for example, a derivative labeled with a fluorophore or the like, a derivative containing a modified nucleotide (e.g., a nucleotide containing a group such as halogen, alkyl such as methyl, alkoxy such as methoxy, thio, or carboxymethyl, and a nucleotide that has undergone base rearrangement, double bond saturation, deamination, replacement of an oxygen molecule with a sulfur molecule, etc.), PNA (peptide nucleic acid; Nielsen, P. E. et al., 1991, Science, Vol. 254, pp. 1497-500), and LNA (locked nucleic acid; Obika, S et al., 1998, Tetrahedron Lett., Vol. 39, pp. 5401-5404).

As used herein, the "nucleic acid" capable of specifically binding to a polynucleotide selected from the prostate cancer marker miRNAs described above or to a complementary strand of the polynucleotide is a synthesized or prepared nucleic acid and, for example, includes a "nucleic acid probe" or a "primer," and is utilized directly or indirectly for detecting the presence or absence of prostate cancer in a subject, for diagnosing the presence or absence or the severity of prostate cancer, the presence or absence or the degree of amelioration of prostate cancer, or the therapeutic sensitivity of prostate cancer, or for screening for a candidate substance useful in prevention, amelioration, or treatment of prostate cancer. The "nucleic acid" includes a nucleotide, an oligonucleotide, and a polynucleotide capable of specifically recognizing and binding to a transcript shown in any of SEQ ID NOs: 1 to 33 or a synthetic cDNA nucleic acid thereof, or a complementary strand thereto in vivo, particularly, in a sample such as a body fluid (e.g., blood or urine), in relation to the development of prostate cancer. The nucleotide, the oligonucleotide, and the polynucleotide can be effectively used as probes for detecting the aforementioned gene expressed in vivo, in tissues, in cells, or the like on the basis of the properties described above, or as primers for amplifying the aforementioned gene expressed in vivo.

The term "detection" used herein is interchangeable with the term "examination," "measurement," or "detection or decision support." As used herein, the term "evaluation" is meant to include diagnosis- or evaluation-support on the basis of examination results or measurement results.

The term "subject" used herein means a mammal such as a primate including a human and a chimpanzee, a pet animal including a dog and a cat, a livestock animal including cattle, a horse, sheep, and a goat, a rodent including a mouse and a rat, and animals raised in a zoo. The subject is preferably a human. Meanwhile, the "healthy subject" also means such a mammal, which is an animal without cancer to be detected. The healthy subject is preferably a human.

The term "prostate cancer" used herein is a malignant tumor developed in the prostate gland, and the term encompasses urothelial carcinoma of the renal pelvis and the urinary tract.

The term "benign prostatic disease" used herein refers to a disease that is diagnosed as a non-malignant tumor (benign) among prostatic diseases that were diagnosed based on comprehensive evaluation of clinical observation including prostatic hyperplasia, prostatitis, urinary incontinence, infections, and high blood PSA levels. The disease is verified to be benign (i.e., the disease is diagnosed to be negative for cancer) when the definitive diagnosis is made as a result of biopsy or other pathological testing.

The term "P" or "P value" used herein refers to a probability at which a more extreme statistic than that actually calculated from data under null hypothesis is observed in a statistical test. Thus, a smaller "P" or "P value" is regarded as being a more significant difference between subjects to be compared.

The term "sensitivity" used herein means a value of (the number of true positives)/(the number of true positives+the number of false negatives). High sensitivity allows prostate cancer to be detected early, which leads to complete resection of cancer regions or a lowered recurrence rate.

The term "specificity" used herein means a value of (the number of true negatives)/(the number of true negatives+the number of false positives). High specificity prevents needless additional testing for healthy subjects misjudged as being prostate cancer patients, which leads to reduction in burden on patients and reduction in medical expense.

The term "accuracy" used herein means a value of (the number of true positives+the number of true negatives)/(the total number of cases). The accuracy indicates the ratio of samples that are identified correctly to all samples and serves as a primary index for evaluating detection performance.

The term "area under the curve (AUC)" indicates an area under the receiver operating characteristic (ROC) curve, which is obtained by plotting sensitivity of certain results on the y-axis and a false positive fraction or (1-specificity) thereof on the x-axis and lowering the discriminant thresholds as parameters. The AUC value lies between 0.5 and 1, and a value closer to 1 indicates a higher discrimination capacity.

As used herein, the "sample" that is subjected to determination, detection, or diagnosis refers to a tissue and a biological material in which the expression of the gene of the present invention varies as prostate cancer develops, as prostate cancer progresses, or as therapeutic effects on prostate cancer are exerted. Specifically, the sample refers to prostate tissue, renal pelvis, urinary tract, lymph node, organs in the vicinity thereof, organs suspected of metastasis, skin, a body fluid such as blood, urine, saliva, sweat, and tissue exudate, serum or plasma prepared from blood, and others such as feces, hair, or the like. The "sample" further refers to a biological sample extracted therefrom, specifically, a gene such as RNA or miRNA.

The term "hsa-miR-1185-2-3p gene" or "hsa-miR-1185-2-3p" used herein includes the hsa-miR-1185-2-3p gene (miRBase Accession No. MIMAT0022713) shown in SEQ ID NO: 1, a homolog or an ortholog of a different organism species, and the like. The hsa-miR-1185-2-3p gene can be obtained by a method described in Berezikov E et al., 2006, Genome Res., Vol. 16, pp. 1289-1298. Also, "hsa-mir-1185-2" (miRBase Accession No. MI0003821; SEQ ID NO: 9) having a hairpin-like structure is known as a precursor of "hsa-miR-1185-2-3p."

The term "hsa-miR-1185-1-3p gene" or "hsa-miR-1185-1-3p" used herein includes the hsa-miR-1185-1-3p gene (miRBase Accession No. MIMAT0022838) shown in SEQ ID NO: 2, a homolog or an ortholog of a different organism species, and the like. The hsa-miR-1185-1-3p gene can be obtained by a method described in Berezikov E et al., 2006, Genome Res., Vol. 16, pp. 1289-1298. Also, "hsa-mir-1185-1" (miRBase Accession No. MI0003844; SEQ ID NO: 10) having a hairpin-like structure is known as a precursor of "hsa-miR-1185-1-3p."

The term "hsa-miR-197-5p gene" or "hsa-miR-197-5p" used herein includes the hsa-miR-197-5p gene (miRBase Accession No. MIMAT0022691) shown in SEQ ID NO: 3, a homolog or an ortholog of a different organism species, and the like. The hsa-miR-197-5p gene can be obtained by a method described in Lagos-Quintana M et al., 2003, RNA, Vol. 9, pp. 175-179. Also, "hsa-mir-197" (miRBase Accession No. MI0000239; SEQ ID NO: 11) having a hairpin-like structure is known as a precursor of "hsa-miR-197-5p."

The term "hsa-miR-6076 gene" or "hsa-miR-6076" used herein includes the hsa-miR-6076 gene (miRBase Accession No. MIMAT0023701) shown in SEQ ID NO: 4, a homolog or an ortholog of a different organism species, and the like. The hsa-miR-6076 gene can be obtained by a method described in Voellenkle C et al., 2012, RNA, Vol. 18, pp. 472-484. Also, "hsa-mir-6076" (miRBase Accession No. M10020353; SEQ ID NO: 12) having a hairpin-like structure is known as a precursor of "hsa-miR-6076."

The term "hsa-miR-17-3p gene" or "hsa-miR-17-3p" used herein includes the hsa-miR-17-3p gene (miRBase Accession No. MIMAT0000071) shown in SEQ ID NO: 5, a homolog or an ortholog of a different organism species, and the like. The hsa-miR-17-3p gene can be obtained by a method described in Lagos-Quintana M et al., 2001, Science, Vol. 294, pp. 853-858. Also, "hsa-mir-17" (miRBase Accession No. MI0000071; SEQ ID NO: 13) having a hairpin-like structure is known as a precursor of "hsa-miR-17-3p."

The term "hsa-miR-320b gene" or "hsa-miR-320b" used herein includes the hsa-miR-320b gene (miRBase Accession No. MIMAT0005792) shown in SEQ ID NO: 6, a homolog or an ortholog of a different organism species, and the like. The hsa-miR-320b gene can be obtained by a method described in Berezikov E et al., 2006, Genome Res., Vol. 16, pp. 1289-1298. Also, "hsa-mir-320b-1 and hsa-mir-320b-2" (miRBase Accession Nos. MI0003776 and MI0003839; SEQ ID NOs: 14 and 15) each having a hairpin-like structure are known as precursors of "hsa-miR-320b."

The term "hsa-miR-6819-5p gene" or "hsa-miR-6819-5p" used herein includes the hsa-miR-6819-5p gene (miRBase Accession No. MIMAT0027538) shown in SEQ ID NO: 7, a homolog or an ortholog of a different organism species, and the like. The hsa-miR-6819-5p gene can be obtained by a method described in Ladewig E et al., 2012, Genome Res., Vol. 22, pp. 1634-1645. Also, "hsa-mir-6819" (miRBase Accession No. MI0022664; SEQ ID NO: 16) having a hairpin-like structure is known as a precursor of "hsa-miR-6819-5p."

The term "hsa-miR-1228-5p gene" or "hsa-miR-1228-5p" used herein includes the hsa-miR-1228-5p gene (miRBase Accession No. MIMAT0005582) shown in SEQ ID NO: 8, a homolog or an ortholog of a different organism species, and the like. The hsa-miR-1228-5p gene can be obtained by a method described in Berezikov E et al., 2007, Mol. Cell, Vol. 28, pp. 328-336. Also, "hsa-mir-1228" (miRBase Accession No. MI0006318; SEQ ID NO: 17) having a hairpin-like structure is known as a precursor of "hsa-miR-1228-5p."

A mature miRNA may become a variant due to the sequence cleaved shorter or longer by one to several flanking nucleotides or due to substitution of nucleotides, when it is cleaved as the mature miRNA from its RNA precursor having a hairpin-like structure. This variant is referred to as isomiR (Morin R D et al., 2008, Genome Res., Vol. 18, pp. 610-621). The miRBase Release 21 shows the nucleotide sequences shown in any of SEQ ID NOs: 1 to 8 as well as a large number of the nucleotide sequence variants and fragments shown in any of SEQ ID NOs: 18 to 33, referred to as isomiRs. These variants can also be obtained as miRNAs each having a nucleotide sequence shown in any of SEQ ID NOs: 1 to 8. Among the variants of polynucleotides comprising the nucleotide sequence shown in any of SEQ ID NOs: 1 to 8 or a nucleotide sequence derived from any of the nucleotide sequences mentioned above by the replacement of u with t according to the present invention, specific examples of the longest variants registered in the miRBase Release 21 include polynucleotides shown in SEQ ID NOs: 18, 20, 22, 24, 26, 28, 30, and 32. Among the variants of polynucleotides comprising the nucleotide sequence shown in any of SEQ ID NOs: 1 to 8 or a nucleotide sequence derived from any of the nucleotide sequences mentioned above by the replacement of u with t according to the present invention, examples of the shortest variants registered in the miRBase Release 21 include polynucleotides shown in SEQ ID NOs: 19, 21, 23, 25, 27, 29, 31, and 33. In addition to these variants and fragments, a large number of isomiR polynucleotides of SEQ ID NOs: 1 to 8 registered in the miRBase are included. Further examples of polynucleotides each comprising a nucleotide sequence shown in any of SEQ ID NOs: 1 to 8 include precursors thereof, which are polynucleotides each shown in any of SEQ ID NOs: 9 to 17.

The names and miRBase Accession Nos. (registration numbers) of the genes shown in SEQ ID NOs: 1 to 33 are shown in Table 1.

As used herein, the expression "capable of specifically binding" refers to a situation in which the nucleic acid probe or primer used in the present invention binds to a specific target nucleic acid and it cannot substantially bind to other nucleic acids.

TABLE 1

| SEQ ID NO | Name of gene | miRBase Accession NO. |
| --- | --- | --- |
| 1 | hsa-miR-1185-2-3p | MIMAT0022713 |
| 2 | hsa-miR-1185-1-3p | MIMAT0022838 |
| 3 | hsa-miR-197-5p | MIMAT0022691 |
| 4 | hsa-miR-6076 | MIMAT0023701 |
| 5 | hsa-miR-17-3p | MIMAT0000071 |
| 6 | hsa-miR-320b | MIMAT0005792 |
| 7 | hsa-miR-6819-5p | MIMAT0027538 |
| 8 | hsa-miR-1228-5p | MIMAT0005582 |
| 9 | hsa-mir-1185-2 | MI0003821 |
| 10 | hsa-mir-1185-1 | MI0003844 |
| 11 | hsa-mir-197 | MI0000239 |
| 12 | hsa-mir-6076 | MI0020353 |
| 13 | hsa-mir-17 | MI0000071 |
| 14 | hsa-mir-320b-1 | MI0003776 |
| 15 | hsa-mir-320b-2 | MI0003839 |
| 16 | hsa-mir-6819 | MI0022664 |
| 17 | hsa-mir-1228 | MI0006318 |
| 18 | isomiR example 1 of SEQ ID NO: 1 | — |
| 19 | isomiR example 2 of SEQ ID NO: 1 | — |
| 20 | isomiR example 1 of SEQ ID NO: 2 | — |
| 21 | isomiR example 2 of SEQ ID NO: 2 | — |
| 22 | isomiR example 2 of SEQ ID NO: 3 | — |
| 23 | isomiR example 1 of SEQ ID NO: 3 | — |
| 24 | isomiR example 2 of SEQ ID NO: 4 | — |
| 25 | isomiR example 1 of SEQ ID NO: 4 | — |
| 26 | isomiR example 2 of SEQ ID NO: 5 | — |
| 27 | isomiR example 1 of SEQ ID NO: 5 | — |
| 28 | isomiR example 2 of SEQ ID NO: 6 | — |
| 29 | isomiR example 1 of SEQ ID NO: 6 | — |
| 30 | isomiR example 1 of SEQ ID NO: 7 | — |
| 31 | isomiR example 2 of SEQ ID NO: 7 | — |
| 32 | isomiR example 1 of SEQ ID NO: 8 | — |
| 33 | isomiR example 2 of SEQ ID NO: 8 | — |

The present specification encompasses the contents disclosed in Japanese Patent Application No. 2018-151952 filed on Aug. 10, 2018, from which the present application claims priority.

Advantageous Effect of Invention

The present invention enables easy detection of prostate cancer with high accuracy. For example, whether or not a subject has prostate cancer can be detected easily with the use of the measured expression level of one or several miRNAs in the blood, serum, and/or plasma that can be collected less invasively from the subject as an indicator.

DESCRIPTION OF EMBODIMENTS

Figure 1:
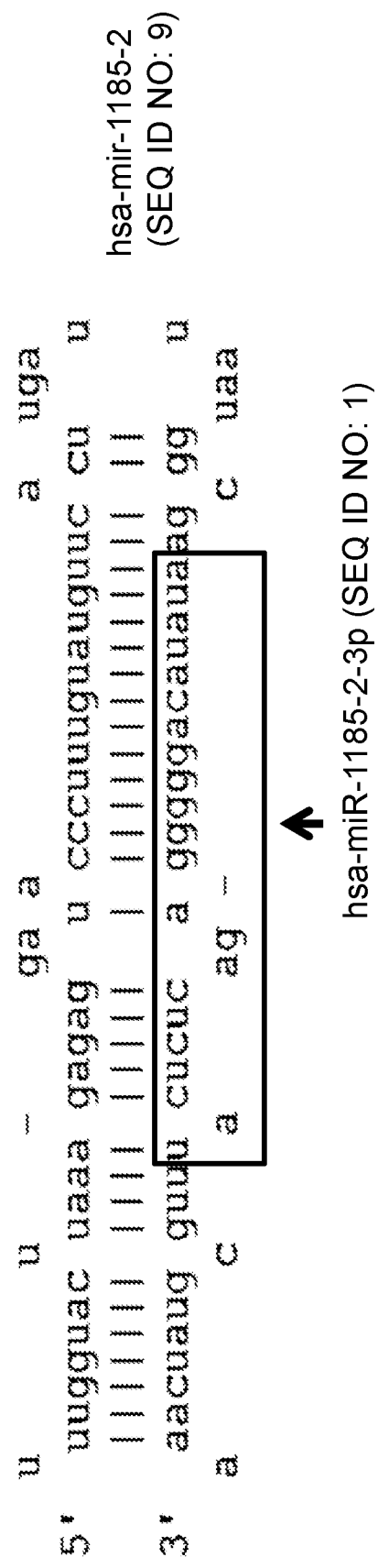
FIG. 1 shows the relationship between the nucleotide sequence of a precursor hsa-mir-1185-2 shown in SEQ ID NO: 9 and the nucleotide sequence of hsa-miR-1185-2-3p shown in SEQ ID NO: 1 which is generated by the sequence of SEQ ID NO: 9.

Hereafter, the present invention is described in detail.

1. Target Nucleic Acid for Prostate Cancer

As the major target nucleic acids as prostate cancer markers for detecting prostate cancer or the presence and/or absence of prostate cancer cells using the nucleic acid probes or primers for detection of prostate cancer as defined above according to the present invention, at least one miRNA selected from the group consisting of miR-1185-2-3p, miR-1185-1-3p, miR-197-5p, miR-6076, miR-17-3p, miR-320b, miR-6819-5p, and miR-1228-5p can also be preferably used.

Examples of the above miRNAs include any human gene comprising any nucleotide sequence shown in any of SEQ III) NOs: 1 to 8 (i.e., hsa-miR-1185-2-3p, hsa-miR-1185-1-3p, hsa-miR-197-5p, hsa-miR-6076, hsa-miR-17-3p, hsa-miR-320b, hsa-miR-6819-5p, and hsa-miR-1228-5p, respectively), a congener thereof, a transcript thereof, and a variant or derivative thereof. Here, the gene, congener, transcript, variant, and derivative are as defined above.

Preferable target nucleic acid is any human gene comprising any nucleotide sequence shown in any of SEQ ID NOs: 1 to 8 or any transcript thereof, and more preferably is the corresponding transcript, namely miRNA and any precursor RNA such as pri-miRNA or pre-miRNA thereof.

The 1st target gene is the hsa-miR-1185-2-3p gene, a congener thereof, a transcript thereof, or a variant or derivative thereof. None of the previously known reports show that change in the expression of the gene or the transcript thereof can serve as a marker for prostate cancer.

The 2nd target gene is the hsa-miR-1185-1-3p gene, a congener thereof, a transcript thereof, or a variant or derivative thereof. None of the previously known reports show that change in the expression of the gene or the transcript thereof can serve as a marker for prostate cancer.

The 3rd target gene is the hsa-miR-197-5p gene, a congener thereof, a transcript thereof, or a variant or derivative thereof. None of the previously known reports show that change in the expression of the gene or the transcript thereof can serve as a marker for prostate cancer.

The 4th target gene is the hsa-miR-6076 gene, a congener thereof, a transcript thereof, or a variant or derivative thereof. None of the previously known reports show that change in the expression of the gene or the transcript thereof can serve as a marker for prostate cancer.

The 5th target gene is the hsa-miR-17-3p gene, a congener thereof, a transcript thereof, or a variant or derivative thereof. The previously known report shows that change in the expression of the gene or the transcript thereof can serve as a marker for prostate cancer (Non-Patent Literature 2).

The 6th target gene is the hsa-miR-320b gene, a congener thereof, a transcript thereof, or a variant or derivative thereof. The previously known report shows that change in the expression of the gene or the transcript thereof can serve as a marker for prostate cancer (Non-Patent Literature 1).

The 7th target gene is the hsa-miR-6819-5p gene, a congener thereof, a transcript thereof, or a variant or derivative thereof. The previously known report shows that change in the expression of the gene or the transcript thereof can serve as a marker for prostate cancer (Patent Literature 2).

The 8th target gene is the hsa-miR-1228-5p gene, a congener thereof, a transcript thereof, or a variant or derivative thereof. The previously known report shows that change in the expression of the gene or the transcript thereof can serve as a marker for prostate cancer (Patent Literature 2).

In one aspect, the present invention relates to a marker for detecting prostate cancer or diagnosing prostate cancer, which comprises at least one selected from the above target nucleic acid.

In one aspect, the present invention relates to use of at least one selected from the above target nucleic acid for detecting prostate cancer or diagnosing prostate cancer.

2. Nucleic Acid Probe or Primer for Detection of Prostate Cancer

A nucleic acid probe or primer that can be used for detection of prostate cancer or diagnosis of prostate cancer according to the present invention enables qualitative and/or quantitative measurement of the presence, expression level, or abundance of the following target nucleic acid for prostate cancer: human-derived miR-1185-2-3p, miR-1185-1-3p, miR-197-5p, miR-6076, miR-17-3p, miR-320b, miR-6819-5p, or miR-1228-5p, or any combination thereof, any congener thereof, any transcript thereof, or any variant or derivative thereof.

The expression level of the above target nucleic acid in subjects having prostate cancer may be increased or decreased (hereinafter, also referred to as an "increase/decrease"), depending on the kind of the target nucleic acid, compared with healthy subjects, benign disease patients, and subjects having cancer other than prostate cancer. Thus, the kit or device of the present invention can be effectively used for detection of prostate cancer by measuring the expression level of the above target nucleic acid in body fluid derived from a subject (e.g., a human) suspected of having prostate cancer and in body fluids derived from healthy subjects, benign disease patients, and patients with cancer other than prostate cancer and then comparing the measured expression level.

A nucleic acid probe or primer that can be used in the present invention is a nucleic acid probe capable of specifically binding to a polynucleotide consisting of a nucleotide sequence shown in at least one selected from SEQ ID NOs: 1 to 4 or a polynucleotide consisting of a nucleotide sequence complementary to the polynucleotide, or a primer for amplifying a polynucleotide consisting of a nucleotide sequence shown in at least one selected from SEQ ID NOs: 1 to 4.

The nucleic acid probes or primers that can be used in the present invention may further comprise a nucleic acid probe capable of specifically binding to a polynucleotide consisting of a nucleotide sequence shown in at least one selected from SEQ ID NOs: 5 to 8 or a polynucleotide consisting of a nucleotide sequence complementary to the polynucleotide, or a primer for amplifying a polynucleotide consisting of a nucleotide sequence shown in at least one selected from SEQ ID NOs: 5 to 8.

In a preferred embodiment of the method of the present invention, the above nucleic acid probe or primer includes any combination of one or more polynucleotides selected from a group of polynucleotides comprising a nucleotide sequence shown in any of SEQ ID NOs: 1 to 33 and a nucleotide sequence derived therefrom by the replacement of u with t, a group of polynucleotides complementary thereto, a group of polynucleotides hybridizing under stringent conditions (described below) to DNA comprising a nucleotide sequence complementary to the former nucleotide sequence, a group of polynucleotides complementary thereto, and a group of polynucleotides comprising 15 or more and preferably 17 or more consecutive nucleotides in the nucleotide sequence of these groups of polynucleotides.

The upper limit of the nucleotide sequence length of these polynucleotides is not particularly limited. When the target nucleic acid is mature miRNA, for example, the number of nucleotides is 30 or less, 28 or less, or 25 or less. When the target nucleic acid is a miRNA precursor, for example, the number of nucleotides is 200 or less, 150 or less, or 120 or less. When the target nucleic acid is isomiR, for example, the number of nucleotides is 40 or less, 35 or less, or 30 or less.

These polynucleotides can be used as nucleic acid probes and primers for detecting target nucleic acids, namely the above prostate cancer markers.

Further, specific examples of the nucleic acid probe or primer that can be used in the present invention include one or more polynucleotides selected from the group consisting of any of the following polynucleotides (a) to (e):

(a) a polynucleotide consisting of a nucleotide sequence shown in any of SEQ ID NOs: 1 to 4 or a nucleotide sequence derived therefrom by the replacement of u with t, a variant thereof, a derivative thereof, or a fragment thereof comprising 15 or more consecutive nucleotides;

(b) a polynucleotide comprising a nucleotide sequence shown in any of SEQ ID NOs: 1 to 4;

(c) a polynucleotide consisting of a nucleotide sequence complementary to a nucleotide sequence shown in any of SEQ ID NOs: 1 to 4 or a nucleotide sequence derived therefrom by the replacement of u with t, a variant thereof, a derivative thereof, or a fragment thereof comprising 15 or more consecutive nucleotides;

(d) a polynucleotide comprising a nucleotide sequence complementary to a nucleotide sequence shown in any of SEQ ID NOs: 1 to 4 or a nucleotide sequence derived therefrom by the replacement of u with t; and (e) a polynucleotide hybridizing under stringent conditions to any of the polynucleotides (a) to (d).

In addition to at least one polynucleotide selected from any of the above polynucleotides (a) to (e), the nucleic acid probe or primer that can be used in the present invention can further comprise a polynucleotide represented by any of the following polynucleotides (1) to (j):

(f) a polynucleotide consisting of a nucleotide sequence shown in any of SEQ ID NOs: 5 to 8 or a nucleotide sequence derived therefrom by the replacement of u with t, a variant thereof, a derivative thereof, or a fragment thereof comprising 15 or more consecutive nucleotides;

(g) a polynucleotide comprising a nucleotide sequence shown in any of SEQ ID NOs: 5 to 8;

(h) a polynucleotide consisting of a nucleotide sequence complementary to a nucleotide sequence shown in any of SEQ ID NOs: 5 to 8 or a nucleotide sequence derived therefrom by the replacement of u with t, a variant thereof, a derivative thereof, or a fragment thereof comprising 15 or more consecutive nucleotides;

(i) a polynucleotide comprising a nucleotide sequence complementary to a nucleotide sequence shown in any of SEQ ID NOs: 5 to 8 or a nucleotide sequence derived therefrom by the replacement of u with t; and (j) a polynucleotide hybridizing under stringent conditions to any of the polynucleotides (f) to (i).

The above polynucleotides or fragments thereof used in the present invention may each be DNA or RNA.

The above polynucleotide that can be used in the present invention may be prepared using a general technique such as DNA recombination technology, a PCR method, or a method using an automated DNA/RNA synthesizer.

As the DNA recombination technology or the PCR method, it is possible to use techniques described in, for example, Ausubel et al., Current Protocols in Molecular Biology, John Willey & Sons, US (1993); and Sambrook et al., Molecular Cloning A Laboratory Manual, Cold Spring Harbor Laboratory Press, US (1989).

The human-derived miR-1185-2-3p, miR-1185-1-3p, miR-197-5p, miR-6076, miR-17-3p, miR-320b, miR-6819-5p, and miR-1228-5p, which are shown in SEQ ID NOs: 1 to 8, are known, and methods for obtaining them are also known, as described above. Therefore, a polynucleotide that can be used as a nucleic acid probe or primer in the present invention can be produced by cloning the gene.

Such a nucleic acid probe or primer may be chemically synthesized using an automated DNA synthesizer. A phosphoramidite process is commonly used for this synthesis, and this process can be used to automatically synthesize a single-stranded DNA with up to about 100 nucleotides in length. The automated DNA synthesizer is commercially available from, for example, Polygen, Inc., ABI, Inc., or Applied BioSystems, Inc.

Alternatively, a polynucleotide of the present invention may be prepared by cDNA cloning. For the cDNA cloning technology, for example, the microRNA Cloning Kit Wako can be utilized.

The sequence of a nucleic acid probe or primer for detection of a polynucleotide consisting of a nucleotide sequence shown in any of SEQ ID NOs: 1 to 8 is not present in vivo as an miRNA or a precursor thereof. For example, the nucleotide sequence shown in SEQ ID NO: 1 is generated from the precursor shown in SEQ ID NO: 9. This precursor has a hairpin-like structure as shown in FIG. 1, and the nucleotide sequence shown in SEQ ID NO: 1 has a mismatch sequence. Accordingly, a nucleotide sequence that is completely complementary to the nucleotide sequence shown in SEQ ID NO: 1 is not naturally occurring in vivo.

Thus, the nucleic acid probe or primer for detecting a nucleotide sequence shown in any of SEQ ID NOs: 1 to 8 may have an artificial nucleotide sequence that is not present in vivo.

3. Kit or Device for Detection of Prostate Cancer

The present invention provides a kit or device for detection of prostate cancer comprising one or more polynucleotide (which may include any variant, fragment, or derivative) that can be used as a nucleic acid probe or primer for measuring a target nucleic acid as a prostate cancer marker in the present invention.

A target nucleic acid as a prostate cancer marker according to the present invention is preferably selected from the following group A.

Group A: miR-1185-2-3p, miR-1185-1-3p, miR-197-5p, and miR-6076.

An additional target nucleic acid that can be optionally used for the measurement is preferably selected from the following group B.

Group B: miR-17-3p, miR-320b, miR-6819-5p, and miR-1228-5p.

The kit or device of the present invention comprises a nucleic acid capable of specifically binding to the above target nucleic acid as prostate cancer marker. Preferably, the kit or device comprises one or more polynucleotides selected from the polynucleotides described in Section 2 above or a variant thereof.

Specifically, the kit or device of the present invention may comprise at least one of a polynucleotide comprising (or consisting of) a nucleotide sequence shown in any of SEQ ID NOs: 1 to 4 or a nucleotide sequence derived therefrom by the replacement of u with t, a polynucleotide comprising (or consisting of) a complementary sequence thereof, a polynucleotide hybridizing under stringent conditions to any of the polynucleotides, or a variant or fragment thereof comprising 15 or more consecutive nucleotides of any of the polynucleotide sequences.

The kit or device of the present invention may further comprise one or more of a polynucleotide comprising (or consisting of) a nucleotide sequence shown in any of SEQ ID NOs: 5 to 8 or a nucleotide sequence derived therefrom by the replacement of u with t, a polynucleotide comprising (or consisting of) a complementary sequence thereof, a polynucleotide hybridizing under stringent conditions to any of the polynucleotides, or a variant or fragment thereof comprising 15 or more consecutive nucleotides of any of the polynucleotide sequences.

A fragment that can be comprised in the kit or device of the present invention may be, for example, one or more polynucleotides and preferably two or more polynucleotides selected from the group consisting of the following (1) and (2):

(1) a polynucleotide comprising 15 or more consecutive nucleotides in a nucleotide sequence derived from the nucleotide sequence shown in any of SEQ ID NOs: 1 to 4 by the replacement of u with t or in a complementary sequence thereof; and (2) a polynucleotide comprising 15 or more consecutive nucleotides in a nucleotide sequence derived from the nucleotide sequence shown in any of SEQ ID NOs: 5 to 8 by the replacement of u with t or in a complementary sequence thereof.

In a preferred embodiment, the polynucleotide is a polynucleotide consisting of a nucleotide sequence shown in any of SEQ ID NOs: 1 to 4 or a nucleotide sequence derived therefrom by the replacement of u with t, a polynucleotide consisting of a complementary sequence thereof, a polynucleotide hybridizing under stringent conditions to any of the polynucleotides, or a variant comprising 15 or more, preferably 17 or more, and more preferably 19 or more consecutive nucleotides of any of the polynucleotides.

In a preferred embodiment, in addition, the polynucleotide is a polynucleotide consisting of a nucleotide sequence shown in any of SEQ ID NOs: 5 to 8 or a nucleotide sequence derived therefrom by the replacement of u with t, a polynucleotide consisting of a complementary sequence thereof, a polynucleotide hybridizing under stringent conditions to any of the polynucleotides, or a variant comprising 15 or more, preferably 17 or more, and more preferably 19 or more consecutive nucleotides of any of the polynucleotides.

In a preferred embodiment, the fragment may be a polynucleotide comprising 15 or more, preferably 17 or more, and more preferably 19 or more consecutive nucleotides.

In the present invention, the size of the polynucleotide fragment is represented by the number of nucleotides in a range of, for example, from 15 to less than the total number of consecutive nucleotides, from 17 to less than the total number of nucleotides, or from 19 to less than the total number of nucleotides in the nucleotide sequence of each polynucleotide.

The upper limit of the nucleotide sequence length of these polynucleotides is not particularly limited. When the target nucleic acid is mature miRNA, for example, the number of nucleotides is 30 or less, 28 or less, or 25 or less. When the target nucleic acid is a miRNA precursor, for example, the number of nucleotides is 200 or less, 150 or less, or 120 or less. When the target nucleic acid is isomiR, for example, the number of nucleotides is 40 or less, 35 or less, or 30 or less.

Specific examples of the above polynucleotide as target nucleic acid in the kit or device of the present invention include 1 or a combination of 2, 3, 4, 5, 6, 7, 8, 9, 10, or more of the above polynucleotides consisting of nucleotide sequences shown in SEQ ID NOs: 1 to 33 listed in Table 1 above. It should be noted that such polynucleotide are merely examples and all other various possible combinations are within the scope of the present invention.

Examples of a combination of target nucleic acids in a kit or device for distinguishing prostate cancer patients from subjects without prostate cancer, such as healthy subjects, patients with benign bone and soft tissue tumor and benign breast disease, and patients with cancer other than prostate cancer in the present invention include a combination of two or more of the above polynucleotides consisting of nucleotide sequences shown in SEQ ID NOs listed in Table 1. Specifically, any two or more of the above polynucleotides consisting of nucleotide sequences shown in SEQ ID NOs: 1 to 8 can be combined. Among them, at least one of the newly found polynucleotides consisting of nucleotide sequences shown in SEQ ID NOs: 1 to 4 is preferably selected. In particular, such combination is preferably a combination including a polynucleotide consisting of a nucleotide sequence shown in SEQ ID NO: 1, more preferably a combination including polynucleotides consisting of nucleotide sequences shown in SEQ ID NOs: 1 to 5, more preferably a combination including polynucleotides consisting of nucleotide sequences shown in SEQ ID NOs: 1, 3, and 5, more preferably a combination including polynucleotides consisting of nucleotide sequences shown in SEQ ID NOs: 2, 5, and 7, more preferably a combination including polynucleotides consisting of nucleotide sequences shown in SEQ ID NOs: 2, 3, 4, and 5, more preferably a combination including polynucleotides consisting of nucleotide sequences shown in SEQ ID NOs: 2, 3, 4, 5, and 8, or more preferably a combination including polynucleotides consisting of nucleotide sequences shown in SEQ ID NOs: 2, 3, 4, 5, and 6.

The kit or device of the present invention may comprise, in addition to the above-described polynucleotide in the present invention (which may include any variant, fragment, or derivative), a polynucleotide known to be able to detect prostate cancer or a polynucleotide that will be discovered in the future.

The kit or device of the present invention may comprise, in addition to the above-described polynucleotides according to the present invention, an antibody (or antibodies) for measuring a known marker for detection of prostate cancer, such as PSA.

These polynucleotides, variants thereof, or fragments thereof contained in the kit of the present invention may be packaged in different containers either individually or in any combination.

The kit of the present invention may comprise a kit for extracting nucleic acids (e.g., total RNA) from body fluids, cells, or tissues, a fluorescent material for labeling, an enzyme and a medium for nucleic acid amplification, an instruction manual, etc.

The device of the present invention may be a device for measuring a cancer marker, in which nucleic acids such as the above-described polynucleotide, variant, derivative, or fragment thereof according to the present invention are, for example, bonded or attached onto a solid phase. Examples of the material for the solid phase include plastics, paper, glass, and silicone. The material for the solid phase is preferably a plastic from the viewpoint of easy processability. The solid phase has any shape and is, for example, square, round, reed-shaped, or film-shaped. The device of the present invention includes, for example, a device for measurement by a hybridization technique. Specific examples thereof include blotting devices and nucleic acid arrays (e.g., microarrays, DNA chips, and RNA chips).

The nucleic acid array technique involves bonding or attaching the nucleic acids one by one by a method, such as a method of spotting the nucleic acids using a high-density dispenser referred to as a spotter or arrayer onto the surface of the solid phase that has been subjected to surface treatment such as coating with L-lysine or introduction of a functional group (e.g., an amino group or a carboxyl group), according to need, a method of spraying the nucleic acids onto the solid phase using an inkjet which injects very small liquid droplets by a piezoelectric element or the like through a nozzle, or a method of sequentially synthesizing nucleotides on the solid phase, to prepare an array such as a chip and measuring target nucleic acids via hybridization using such array.

The kit or device of the present invention comprises nucleic acids capable of specifically binding to at least one, preferably at least two, more preferably at least three, and most preferably all polynucleotides selected from the aforementioned prostate cancer marker miRNAs of the group A, or a polynucleotide consisting of a nucleotide sequence complementary to the polynucleotide, respectively. The kit or device of the present invention can optionally further comprise nucleic acids capable of specifically binding to at least one, preferably at least two, more preferably at least three, and most preferably all polynucleotides selected from the aforementioned prostate cancer marker miRNAs of the group B, or a polynucleotide consisting of a nucleotide sequence complementary to the polynucleotide, respectively.

The kit or device of the present invention can be used for detecting prostate cancer as described in Section 4 below.

4. Method for Detecting Prostate Cancer

The present invention further relates to a method for detecting prostate cancer comprising measuring, in vitro, 1 or more expression levels (e.g., expression profiles) of prostate cancer-derived genes represented by miR-1185-2-3p, miR-1185-1-3p, miR-197-5p, and miR-6076, and optionally expression levels of prostate cancer-derived genes represented by miR-17-3p, miR-320b, miR-6819-5p, and miR-1228-5p in a sample and evaluating, in vitro, whether or not a subject has prostate cancer using the measured expression level (and optionally a control expression level in a healthy subject measured in the same manner). This method comprises, for example, using the expression level of the aforementioned genes in a sample collected from a subject suspected of having prostate cancer (e.g., blood, serum, or plasma) and the control gene expression levels in samples collected from subjects without prostate cancer (e.g., blood, serum, or plasma) (e.g., such gene expression levels may be compared). When a difference is observed in the expression level of the target nucleic acid in the samples, the subject can be determined to have prostate cancer.

The aforementioned method of the present invention enables early diagnosis of prostate cancer in a low-invasive manner with high sensitivity and specificity. This allows early treatment and improved prognosis and further enables observation of disease exacerbation and observation of effectiveness of surgical, radiotherapeutic, and chemotherapeutic treatment.

For the method for extracting the prostate cancer-derived gene from the sample such as blood, serum, or plasma according to the present invention, it is particularly preferable to add a reagent for RNA extraction in 3D-Gene (registered trademark) RNA extraction reagent from liquid sample kit (Toray Industries, Inc., Japan) to prepare a sample. Alternatively, a general acidic phenol method (an acid guanidinium-phenol-chloroform (AGPC) method) may be used, or Trizol (registered trademark) (Life Technologies Corp.) may be used. Alternatively, a reagent for RNA extraction containing acidic phenol, such as Trizol (Life Technologies Corp.) or Isogen (Nippon Gene Co., Ltd., Japan), may be added to prepare a sample. In addition, a kit such as miRNeasy (registered trademark) Mini Kit (Qiagen) may be used, although the method is not limited thereto.

The present invention also provides use of a prostate cancer-derived miRNA gene in a sample from a subject for in vitro detection of an expression product thereof.

A technique for carrying out the method of the present invention is not limited. For example, the kit or device of the present invention (comprising the above nucleic acid that can be used in the present invention) as described in Section 3 above may be used. The method of the present invention involves the use of the kit or device comprising a single polynucleotide or any possible combination of polynucleotides that can be used in the present invention, as described above.

In the detection or (genetic) diagnosis of prostate cancer according to the present invention, a polynucleotide contained in the kit or device of the present invention can be used as a probe or a primer. When using polynucleotide as a primer, TaqMan (registered trademark) MicroRNA Assays (Life Technologies Corp.), miScript PCR System (Qiagen), or the like can be used, although the present invention is not limited thereto.

In the method of the present invention, measurement of the gene expression levels can be performed according to a conventional technique known in the art that specifically detects particular genes. Examples thereof include hybridization techniques, such as Northern blotting, Southern blotting, in situ hybridization, Northern hybridization, and Southern hybridization, a quantitative amplification technique such as quantitative RT-PCR, and a method involving the use of a next-generation sequencer. A body fluid such as blood, serum, plasma, or urine from a subject is collected as a sample to be assayed depending on the type of the detection method to be used. Alternatively, total RNA prepared from such a body fluid by the method described above may be used, and various polynucleotides including cDNA prepared from the RNA may be used.

The method of the present invention is useful for diagnosis of prostate cancer or detection of the presence or absence of prostate cancer. Specifically, detection of prostate cancer according to the present invention can be performed by detecting in vitro an expression level of a gene, which is detected using the nucleic acid probe or primer contained in the kit or the device according to the present invention, in a sample such as blood, serum, plasma, or urine from a subject suspected of having prostate cancer. If the expression level of a polynucleotide consisting of a nucleotide sequence shown in at least one of SEQ ID NOs: 1 to 4 and optionally a nucleotide sequence shown in one or more of SEQ ID NOs: 5 to 8 in a sample such as blood, serum, plasma, or urine of a subject suspected of having prostate cancer, is statistically significantly higher than an expression level thereof in a sample such as blood, serum, or plasma, or urine of a subject without prostate cancer, the former subject can be evaluated as having prostate cancer.

Regarding the method of the present invention, the method for detecting the presence or absence of prostate cancer in a sample from a subject comprises collecting a body fluid such as blood, serum, plasma, or urine of the subject, and measuring the expression level of the target gene (or target nucleic acid) contained therein using one or more polynucleotides (including a variant, fragment, or derivative) selected from the groups of polynucleotides according to the present invention, thereby evaluating the presence or absence of prostate cancer or detecting prostate cancer.

The method for detecting prostate cancer according to the present invention can be performed in combination with other prostate cancer-related tests, such as rectal examination, transrectal ultrasonography of the prostate, biopsy, or imaging tests, such as CT, MRI, and bone scintigraphy, aimed at, for example, more precise diagnosis of prostate cancer in a prostate cancer patient. In addition, the method of the present invention can be performed prior to such testing in order to evaluate the necessity for performance of such prostate cancer-related tests.

The method for detecting prostate cancer according to the present invention can be employed for evaluation or diagnosis as to presence or absence of remediation of prostate cancer or an extent of remediation when, for example, a prostate cancer patient is subjected to treatment or remediation of prostate cancer by means of prostate cancer-related treatment techniques that are known or in the development stage (examples of such treatment techniques include, but are not limited to: radiation treatment techniques, such as x-ray, proton beam, and heavy particle therapy, and high-dose rate interstitial radiation and permanent brachytherapy among radiation treatment techniques; hormonal treatment techniques using luteinizing hormone releasing factor (LH- RH) agonists, such as goserelin acetate and leuprorelin acetate, anti-androgen drugs, such as chlormadinone acetate, flutamide, picartamide, enzalutamide, and abiraterone acetate, LH-RH antagonists, such as degarelix acetate, and estrogen, such as ethinyl estradiol; chemotherapy techniques using drugs, such as docetaxel hydrate, cabazitaxel, and estramustine phosphate sodium hydrate; and use of such treatment techniques in adequate combination).

Another aspect of the present invention provides a method for treatment of prostate cancer. Specifically, the method for treatment of prostate cancer according to the present invention comprises a step of performing the treatment of prostate cancer (radiation treatment, hormonal treatment, chemotherapy, and use of such treatment techniques in combination) on a subject who is determined to have prostate cancer as a result of the method of detection described above.

The method of the present invention may comprise, for example, the following steps (a), (b), and (c):
  (a) bringing, in vitro, a sample from a subject into contact with a polynucleotide contained in the kit or device of the present invention;
  (b) measuring an expression level of a target nucleic acid in the sample using the polynucleotide as a nucleic acid probe or primer; and
  (c) evaluating the presence or absence of prostate cancer (cells) in the subject on the basis of the measurement results in step (b).

In one embodiment, the present invention provides a method for detecting prostate cancer comprising measuring an expression level of a target nucleic acid in a sample from a subject using a nucleic acid capable of specifically binding to at least one, and preferably at least two polynucleotides selected from the group consisting of miR-1185-2-3p, miR-1185-1-3p, miR-197-5p, and miR-6076, or a polynucleotide consisting of a nucleotide sequence complementary to the polynucleotide; and evaluating in vitro whether or not the subject has prostate cancer using the measured expression level and a control expression level in a subject without prostate cancer measured in the same manner.

The term "evaluating" as used herein is evaluation support based on the results of in vitro examination, which is not physician's judgment.

In the method of the present invention, specifically, miR-1185-2-3p is hsa-miR-1185-2-3p, miR-1185-1-3p is hsa-miR-1185-1-3p, miR-197-5p is hsa-miR-197-5p, and miR-6076 is hsa-miR-6076, as described above.

In one embodiment, in addition, a nucleic acid (specifically, a probe or primer) in the method of the present invention is selected from the group consisting of the following polynucleotides (a) to (e):
  (a) a polynucleotide consisting of a nucleotide sequence shown in any of SEQ ID NOs: 1 to 4 or a nucleotide sequence derived therefrom by the replacement of u with t, a variant thereof, a derivative thereof, or a fragment thereof comprising 15 or more consecutive nucleotides;
  (b) a polynucleotide comprising a nucleotide sequence shown in any of SEQ ID NOs: 1 to 4;
  (c) a polynucleotide consisting of a nucleotide sequence complementary to a nucleotide sequence shown in any of SEQ ID NOs: 1 to 4 or a nucleotide sequence derived therefrom by the replacement of u with t, a variant thereof, a derivative thereof, or a fragment thereof comprising 15 or more consecutive nucleotides;
  (d) a polynucleotide comprising a nucleotide sequence complementary to a nucleotide sequence shown in any of SEQ ID NOs: 1 to 4 or a nucleotide sequence derived therefrom by the replacement of u with t; and
  (e) a polynucleotide hybridizing under stringent conditions to any of the polynucleotides (a) to (d).

In the method of the present invention, further, the expression level of at least one polynucleotide selected from the group consisting of miR-17-3p, miR-320b, miR-6819-5p, and miR-1228-5p can be measured.

Specifically, miR-17-3p is hsa-miR-17-3p, miR-320b is hsa-miR-320b, miR-6819-5p is hsa-miR-6819-5p, and miR-1228-5p is hsa-miR-1228-5p.

In one embodiment, in addition, the expression level of the polynucleotide are measured using nucleic acid capable of specifically binding to the polynucleotide or polynucleotide comprising nucleotide sequence complementary to the polynucleotide, and the nucleic acid are polynucleotide selected from the group consisting of the following polynucleotides (f) to (j):
  (f) a polynucleotide consisting of a nucleotide sequence shown in any of SEQ ID NOs: 5 to 8 or a nucleotide sequence derived therefrom by the replacement of u with t, a variant thereof, a derivative thereof; or a fragment thereof comprising 15 or more consecutive nucleotides;
  (g) a polynucleotide comprising a nucleotide sequence shown in any of SEQ ID NOs: 5 to 8;
  (h) a polynucleotide consisting of a nucleotide sequence complementary to a nucleotide sequence shown in any of SEQ ID NOs: 5 to 8 or a nucleotide sequence derived therefrom by the replacement of u with t, a variant thereof, a derivative thereof, or a fragment thereof comprising 15 or more consecutive nucleotides;
  (i) a polynucleotide comprising a nucleotide sequence complementary to a nucleotide sequence shown in any of SEQ ID NOs: 5 to 8 or a nucleotide sequence derived therefrom by the replacement of u with t; and
  (j) a polynucleotide hybridizing under stringent conditions to any of the polynucleotides (f) to (i).

The upper limit of the nucleotide sequence length of these polynucleotides is not particularly limited. When the target nucleic acid is mature miRNA, for example, the number of nucleotides is 30 or less, 28 or less, or 25 or less. When the target nucleic acid is a miRNA precursor, for example, the number of nucleotides is 200 or less, 150 or less, or 120 or less. When the target nucleic acid is isomiR, for example, the number of nucleotides is 40 or less, 35 or less, or 30 or less.

Examples of the sample used in the method of the present invention can include samples prepared from living tissues (preferably prostate tissues, renal pelvis, or urinary tract tissues) or body fluids such as blood, serum, plasma, and urine from subjects. Specifically, an RNA-containing sample prepared from the tissue, a polynucleotide-containing sample further prepared therefrom, a body fluid such as blood, serum, plasma, or urine, a portion or the whole of a living tissue collected from the subject via biopsy or other means, a living tissue excised by surgery, or the like can be used, and the sample for measurement can be prepared therefrom.

The term "subject" used herein refers to a mammal, such as a human, a monkey, a mouse, or a rat, with a human being preferable, although the subject is not limited thereto.

The steps of the method of the present invention can be changed depending on the type of the sample to be measured.

When using RNA as an analyte, the method for detecting prostate cancer (cells) can comprise, for example, the following steps (a), (b), and (c):
  (a) binding RNA prepared from a sample from a subject (wherein, for example, the 3' end of the RNA may be polyadenylated for quantitative RT-PCR in step (b) or any sequence may be added to one or both ends of the RNA by ligation) or a complementary polynucleotides (cDNA) transcribed from the RNA to a polynucleotide in the kit of the present invention;

(b) measuring the sample-derived RNA or the cDNA synthesized from the RNA, which has been bound to the polynucleotide, by hybridization using the polynucleotide as a nucleic acid probe or by quantitative RT-PCR using the polynucleotide as a primer; and (c) evaluating the presence or absence of prostate cancer (or the prostate cancer-derived gene) on the basis of the measurement results of step (b).

For example, various hybridization methods can be used for measuring the expression level of a target gene according to the present invention. Examples of hybridization methods that can be used include Northern blotting, Southern blotting, DNA chip analysis, in situ hybridization, Northern hybridization, and Southern hybridization. PCR such as quantitative RT-PCR or next-generation sequencing can also be used in combination with or alternative to the hybridization method.

When using Northern blotting, the presence or absence of expression of each gene or the expression level thereof in the RNA can be detected or measured using, for example, the nucleic acid probe that can be used in the present invention. A specific example thereof is a method, which comprises labeling the nucleic acid probe (or a complementary strand) with a radioisotope ($^{32}$P, $^{33}$P, $^{35}$S, etc.) or a fluorescent material, hybridizing the labeled product with the living tissue-derived RNA from a subject, which is transferred to a nylon membrane in accordance with a conventional technique, and then detecting and measuring a signal derived from the label (a radioisotope or fluorescent material) on the formed DNA/RNA double strand using a radiation detector (e.g., BAS-1800 II, Fujifilm Corp.) or a fluorescence detector (e.g., STORM 865, GE Healthcare Japan Corp.).

When using quantitative RT-PCR, the presence or absence of expression of each gene or the expression level thereof in the RNA can be detected or measured using, for example, the primer that can be used in the present invention. A specific example thereof is a method, which comprises collecting the living tissue-derived RNA from a subject, polyadenylating the 3'-end, preparing cDNAs from the polyadenylated RNA in accordance with a conventional method, performing PCR in accordance with a conventional method by hybridizing a pair of primers (consisting of a plus strand and a reverse strand each binding to the cDNA) that could be contained in the kit or device for detection of the present invention with the cDNA, so as to amplify the region of each target gene marker with the cDNA as a template, and detecting the obtained single-stranded or double-stranded DNA. The method for detecting the single-stranded or double-stranded DNA can include a method of performing the PCR using the primers labeled in advance with a radioisotope or a fluorescent material, a method of electrophoresing the PCR product on an agarose gel and staining the double-stranded DNA with ethidium bromide or the like for detection, and a method of transferring the produced single-stranded or double-stranded DNA to a nylon membrane or the like in accordance with a conventional method and hybridizing the single-stranded or double-stranded DNA with a labeled nucleic acid probe for detection.

When using quantitative RT-PCR, a commercially available kit for measurement specially designed for quantitative measurement of miRNA, such as TaqMan (registered trademark) MicroRNA Assays (Life Technologies Corp.), LNA (registered trademark)-based MicroRNA PCR (Exiqon), or Ncode (registered trademark) miRNA qRT-PCT kit (Invitrogen Corp.), may be used.

When using nucleic acid array analysis, for example, an RNA chip or a DNA chip in which the kit or device for detection in the present invention is attached as nucleic acid probes (single-stranded or double-stranded) to a substrate (solid phase) is used. Regions comprising the nucleic acid probes attached thereto are referred to as probe spots, and regions comprising no nucleic acid probes attached thereto are referred to as blank spots. A group of genes immobilized on a solid-phase substrate is generally referred to as a nucleic acid chip, a nucleic acid array, a microarray, or the like. The DNA or RNA array includes a DNA or RNA macroarray and a DNA or RNA microarray. In the present specification, the term "chip" includes these arrays. 3D-Gene (registered trademark) Human miRNA Oligo chip (Toray Industries, Inc., Japan) can be used as the DNA chip, although the DNA chip is not limited thereto.

Examples of the measurement using the DNA chip can include, but are not limited to, a method of detecting and measuring a signal derived from the label on the kit or device for detection using an image detector (e.g., Typhoon 9410, GE Healthcare, and 3D-Gene (registered trademark) scanner, Toray Industries, Inc., Japan).

Under the "stringent conditions" used herein, as described above, a nucleic acid probe hybridizes to its target sequence to a detectably larger extent (e.g., a measurement value equal to or larger than "(a mean of background measurement values)+(a standard error of the background measurement values)×2)") than that for other sequences.

The stringent conditions are defined by hybridization and subsequent washing. Examples of the hybridization conditions include, but are not limited to, 30° C. to 60° C. for 1 to 24 hours in a solution containing SSC, a surfactant, formamide, dextran sulfate, a blocking agent, etc. In this context, 1×SSC is an aqueous solution (pH 7.0) containing 150 mM sodium chloride and 15 mM sodium citrate. The surfactant includes, for example, SDS (sodium dodecyl sulfate), Triton, or Tween. The hybridization conditions more preferably comprise 3-10×SSC and 0.1-1% SDS. Examples of the conditions for the washing, following the hybridization, which is another condition to define the stringent conditions, can include conditions comprising continuous washing at 30° C. in a solution containing 0.5×SSC and 0.1% SDS, at 30° C. in a solution containing 0.2×SSC and 0.1% SDS, and at 30° C. in a 0.05×SSC solution. It is desirable that the complementary strand remain hybridized to a target plus strand even washed under such conditions. Specific examples of such complementary strand can include a strand consisting of a nucleotide sequence in a completely complementary relationship with the nucleotide sequence of the target plus (+) strand, and a strand consisting of a nucleotide sequence having at least 80%, preferably at least 85%, more preferably at least 90%, or at least 95% homology (identity) to the strand.

Other examples of the "stringent conditions" for the hybridization are described in, for example, Sambrook, J. & Russel, D., Molecular Cloning, A LABORATORY MANUAL, Cold Spring Harbor Laboratory Press, published on Jan. 15, 2001, Vol. 1, 7.42 to 7.45 and Vol. 2, 8.9 to 8.17, and can be used in the present invention.

Examples of the conditions for carrying out PCR using polynucleotide fragments in the kit of the present invention as primers include treatment for approximately 15 seconds to 1 minute at 5 to 10° C. plus a Tm value calculated from the sequences of the primers using a PCR buffer having a composition such as 10 mM Tris-HCL (pH 8.3), 50 mM KCl, and 1 to 2 mM $MgCl_2$. Examples of the method for calculating such a Tm value include Tm value=2×(the number of adenine residues+the number of thymine residues)+4×(the number of guanine residues+the number of cytosine residues).

In the method of the present invention, measurement of the target gene expression level may be performed with a sequencer, in addition to the hybridization methods described above. When using a sequencer, any of DNA sequencers of the first generation based on the Sanger method, the second generation with a shorter read size, and the third generation with a longer read size can be used (referred to as the "next-generation sequencer," including sequencers of the second generation and the third generation herein). A commercially available measurement kit specially designed for measurement of miRNA may be used with the use of, for example, Miseq, Hiseq, or NexSeq (Illumina, Inc.), Ion Proton, Ion PGM, or Ion S5/S5 XL (Thermo Fisher Scientific Inc.), PacBio RS II or Sequel (Pacific Biosciences of California, Inc.), or, when using a Nanopore sequencer, MinION (Oxford Nanopore Technologies Ltd.).

Next-generation sequencing is a method of obtaining sequence information using a next-generation sequencer, which is characterized in that a significantly larger number of sequencing reactions can be simultaneously performed, compared with the Sanger method (e.g., Rick Kamps et al., Int. J. Mol. Sci., 2017, 18(2), p. 308 and Int. Neurourol. J., 2016, 20 (Supp 1.2), S76-83). Examples of next-generation sequencing steps for miRNA include, but are not limited to, the following steps: at the outset, adaptor sequences having predetermined nucleotide sequences are attached, and all RNAs are reverse-transcribed into cDNAs before or after attachment of the sequences. After the reverse transcription, cDNAs derived from specific target miRNAs may be amplified or concentrated by PCR or other means or with a probe or the like, so as to analyze the target miRNA before sequencing steps. While details of subsequent sequencing steps vary depending on the type of a next-generation sequencer, typically, a sequencing reaction is performed by linking the sequence of interest to a substrate via an adaptor sequence and further using the adaptor sequence as a priming site. Concerning the details of the sequencing reaction, a reference may be made to, for example, Rick Kamps et al. (see supra). In the end, the data are outputted. This step provides a collection of sequence information (reads) obtained by the sequencing reaction. For example, next-generation sequencing enables identification of a target miRNA based on the sequence information and measurement of the expression level thereof based on the number of reads having the sequences of the target miRNA.

In the present invention, gene expression levels can be calculated via statistical treatment described in, for example, Statistical analysis of gene expression microarray data (Speed T., Chapman and Hall/CRC), and A beginner's guide: Microarray gene expression data analysis (Causton H. C. et al., Blackwell publishing), although the method of calculation is not limited thereto. For example, 2 times, preferably 3 times, and more preferably 6 times the standard deviation of the measurement values of the blank spots are added to the average measurement value of the blank spots on the DNA chip, and probe spots having a signal value equal to or larger than the resulting value can be regarded as detection spots. Alternatively, the average measurement value of the blank spots is regarded as a background and can be subtracted from the measurement values of the probe spots to determine gene expression levels. A missing value for a gene expression level can be excluded from the analyte, preferably replaced with the smallest value of the gene expression level in each DNA chip, or more preferably replaced with a value obtained by subtracting 0.1 from a logarithmic value of the smallest value of the gene expression level. In order to eliminate low-signal genes, only a gene having a gene expression level of $2^6$, preferably $2^8$, and more preferably $2^{10}$ or larger in 20% or more, preferably 50% or more, and more preferably 80% or more of the number of measurement samples can be selected as the analyte. Examples of the normalization of the gene expression level include, but are not limited to, global normalization and quantile normalization (Bolstad, B. M. et al., 2003, Bioinformatics, Vol. 19, pp. 185-193). Further examples of methods include: a method in which endogenous genes exhibiting constitutive expression levels regardless of samples are identified as control samples and used for normalization; and a method in which a given amount of particular nucleic acids are added externally and the amount thereof is used for normalization.

The present invention also provides a method for detecting prostate cancer (or assisting the detection thereof) in a subject comprising: measuring target gene expression levels in a sample from the subject; and assigning the expression levels of the target genes in the sample from the subject to a discriminant (discriminant function), which is prepared using gene expression levels of a sample from a subject (or a patient) known to have prostate cancer and a sample from a subject without prostate cancer, as a training sample, and is capable of distinguishing the presence or absence of prostate cancer, thereby evaluating the presence or absence of prostate cancer.

Specifically, the present invention further provides the method comprising: a first step of measuring in vitro expression levels of target genes in a plurality of samples from subjects known to be with prostate cancer and/or without prostate cancer; a second step of preparing a discriminant formula using the measured expression levels of the target genes obtained in the first step as training samples; a third step of measuring in vitro the expression levels of the target genes in a sample from the subject in the same manner as in the first step; and a fourth step of assigning the measured expression levels of the target genes obtained in the third step to the discriminant formula obtained in the second step, and determining or evaluating whether or not the subject has prostate cancer on the basis of the results obtained from the discriminant formula. The above target genes are those that can be detected, for example, by the polynucleotides, the polynucleotides contained in the kit or chip, and variants thereof or fragments thereof.

The discriminant formulae herein can be prepared with the use of any discriminant analysis methods, based on which a discriminant formula that distinguishes the presence or absence of prostate cancer can be prepared, such as Fisher's discriminant analysis, nonlinear discriminant analysis based on the Mahalanobis' distance, neural network, Support Vector Machine (SVM), logistic regression analysis (especially, logistic regression analysis using the LASSO (Least Absolute Shrinkage and Selection Operator)), k-nearest neighbor method, or decision tree, although the analysis method is not limited to these specific examples.

When a clustering boundary is a straight line or a hyperplane, the linear discriminant analysis is a method for determining the belonging of a cluster using Formula 1 as a discriminant formula. In Formula 1, "x" represents an explanatory variable, w represents a coefficient of the explanatory variable, and $w_0$ represents a constant term.

$$f(x) = w_0 + \sum_{i=1}^{N} w_i x_i \quad \text{Formula 1}$$

Values obtained from the discriminant formula are referred to as discriminant scores. The measurement values of a newly offered data set can be assigned as explanatory variables to the discriminant formula to determine clusters by the signs of the discriminant scores.

The Fisher's discriminant analysis, a type of linear discriminant analysis, is a dimensionality reduction method for selecting a dimension suitable for discriminating classes, and constructs a highly discriminating synthetic variable by focusing on the variance of the synthetic variables and minimizing the variance of data having the same label (Venables, W. N. et al., Modern Applied Statistics with S. Fourth edition. Springer., 2002). In the Fisher's discriminant analysis, direction w of projection is determined so as to maximize Formula 2. In this formula, μ represents an average input, $n_g$ represents the number of data belonging to class g, and $\mu_g$ represents an average input of the data belonging to class g. The numerator and the denominator are the interclass variance and the intraclass variance, respectively, when each of data is projected in the direction of the vector w. Discriminant coefficient wi is determined by maximizing this ratio (Takafumi Kanamori et al., "Pattern Recognition," KYORITSU SHUPPAN CO., LTD. (Tokyo, Japan) (2009); Richard O. et al., Pattern Classification, Second Edition., Wiley-Interscience, 2000).

$$J(w) = \frac{\sum_{g=1}^{G} n_g (w^T \mu_g - w^T \mu)(w^T \mu_g - w^T \mu)^T}{\sum_{g=1}^{G} \sum_{i:y_i=g} (w^T x_i - w^T \mu_g)(w^T x_i - w^T \mu_g)} \quad \text{Formula 2}$$

subject to $$\mu = \sum_{i=1}^{n} \frac{x_i}{n},$$

$$\mu_g = \sum_{i:u_i=g}^{n} \frac{x_i}{n_g}$$

The Mahalanobis' distance is calculated according to Formula 3 in consideration of data correlation and can be used as nonlinear discriminant analysis for determining a cluster in which a data point belongs to, based on a short Mahalanobis' distance from the data point to that cluster. In Formula 3, μ, represents a central vector of each cluster, and $S^{-1}$ represents an inverse matrix of the variance-covariance matrix of the cluster. The central vector is calculated from explanatory variable x, and an average vector, a median value vector, or the like can be used.

$$D(x, \mu) = \{(x-\mu)^t S^{-1}(x-\mu)\}^{\frac{1}{2}} \quad \text{Formula 3}$$

SVM is a discriminant analysis method devised by V. Vapnik (The Nature of Statistical Leaning Theory, Springer, 1995). Particular data points of a data set having known classes are defined as explanatory variables, and classes are defined as objective variables. A boundary plane referred to as a hyperplane for correctly classifying the data set into the known classes is determined, and a discriminant formula for data classification is determined using the boundary plane. Then, the measurement values of a newly offered data set can be assigned as explanatory variables to the discriminant formula to determine classes. In this respect, the result of the discriminant analysis may be classes, a probability of being classified into appropriate classes, or the distance from the hyperplane. In SVM, a method of nonlinearly converting a feature vector to a high dimension and performing linear discriminant analysis in the space is known as a method for tackling nonlinear problems. An expression in which an inner product of two factors in a nonlinearly mapped space is expressed only by inputs in their original spaces is referred to as "kernel." Examples of the kernel can include a linear kernel, an RBF (Radial Basis Function) kernel, and a Gaussian kernel. While highly dimensional mapping is performed according to the kernel, the optimum discriminant formula, i.e., a discriminant formula, can be actually constructed by merely calculating the kernel while avoiding calculation of features in the mapped space (e.g., Hideki Aso et al., Frontier of Statistical Science 6 "Statistics of pattern recognition and learning—New concepts and approaches," Iwanami Shoten, Publishers (Tokyo, Japan) (2004); Nello Cristianini et al., Introduction to SVM, Kyoritsu Shuppan Co., Ltd. (Tokyo, Japan) (2008)).

C-support vector classification (C-SVC), a type of SVM, comprises preparing a hyperplane by training a data set with the explanatory variables of two groups and classifying an unknown data set into either of the groups (C. Cortes et al., 1995, Machine Learning, Vol. 20, pp. 273-297).

Exemplary calculation of the C-SVC discriminant formula that can be used in the method of the present invention will be given below. First, all subjects are divided into two groups, i.e., a group of prostate cancer patients and a group of subjects without prostate cancer. For example, a prostate tissue test can be used as a reference of determining whether or not a subject has prostate cancer.

Next, a data set consisting of comprehensive gene expression levels of serum-derived samples of the two divided groups (hereinafter, this data set is referred to as a training cohort) is prepared, and a C-SVC discriminant formula is determined using genes found to differ clearly in their gene expression levels between the two groups as explanatory variables and this grouping as objective variables (e.g., −1 and +1). An optimizing objective function is represented by Formula 4, wherein "e" represents all input vectors, "y" represents an objective variable, "a" represents a Lagrange's undetermined multiplier vector, "Q" represents a positive definite matrix, and "C" represents a parameter for adjusting constrained conditions.

$$\min_{a} \frac{1}{2} a^T Q a - e^T a \quad \text{Formula 4}$$

subject to $$y^T a = 0,$$

$$0 \leq a_i \leq C,$$

$$i = 1, \ldots, i,$$

Formula 5 is a finally obtained discriminant formula, and a group to which the data point belongs can be determined on the basis of the sign of a value obtained according to the discriminant formula. In this formula, "x" represents a support vector, "y" represents a label indicating the belonging of a group, "a" represents the corresponding coefficient, "b" represents a constant term, and "K" represents a kernel function.

$$f(x) = \text{sgn}\left(\sum_{i=1}^{l} y_i a_i K(x_i, x) + b\right) \quad \text{Formula 5}$$

For example, an RBF kernel defined by Formula 6 can be used as the kernel function. In this formula, "x" represents a support vector, and "y" represents a kernel parameter for adjusting the complexity of the hyperplane.

$$K(x_i, x_j) = \exp(-r\|x_i - x_j\|^2), r < 0 \quad \text{Formula 6}$$

Logistic regression is a multivariate analysis method in which one category variable (binary variable) is used as an objective variable to predict the probability of occurrence using multiple explanatory variables, which is represented by Formula 7 below.

$$\log \text{it}(\text{prob}(y_i=1)) = \beta_0 + \Sigma_{j=1}^{P} \beta_j \chi_j \quad \text{Formula 7}$$

The LASSO (Least Absolute Shrinkage and Selection Operator) method is one of techniques for selecting and adjusting variables when multiple variables are observed, which was proposed by Tibshirani (Tibshirani R., 1996, J. R. Stat. Soc. Ser. B, Vol. 58, pp. 267-88). The LASSO method is characterized in that penalties are imposed upon estimation of regression coefficients, so that overfitting to a model is suppressed and some of the regression coefficients are then estimated to be 0. In logistic regression using the LASSO method, regression coefficients are estimated so as to maximize a log-likelihood function represented by Formula 8.

$$\frac{1}{N}\sum_{i=1}^{N}\left(y_i(\beta_0 + x_j^T\beta) - \log\left(1 + e^{(\beta_0 + x_j^T\beta)}\right)\right) - \lambda\sum_{j=1}^{P}|\beta_j| \quad \text{Formula 8}$$

The value y of the discriminant formula obtained in analysis by the LASSO method is assigned to the logistic function represented by Formula 9 below, and the group to which the subject belongs can be determined on the basis of the obtained value.

$$\text{Exp}(y)/(1+\exp(y)) \quad \text{Formula 9}$$

The method of the present invention can comprise, for example, the following steps (a), (b), and (c):

(a) measuring an expression level of a target gene in samples already known to be from prostate cancer patients and to be from subjects without prostate cancer, using polynucleotide, a kit, or a DNA chip for detection according to the present invention;

(b) preparing the discriminant formulae 1 to 3, 5, 6, and 9 described above based on the expression level measured in step (a); and (c) measuring an expression level of the target gene in a sample from a subject using the polynucleotide, the kit, or the device (e.g., a DNA chip) for diagnosis (detection) according to the present invention, assigning the obtained measurement value to the discriminants prepared in step (b), and determining or evaluating whether or not the subject has prostate cancer on the basis of the obtained results or evaluating the expression level derived from a prostate cancer patient in comparison with a control from a subject without prostate cancer.

In the discriminant formulae 1 to 3, 5, 6, and 9, "x" represents an explanatory variable and includes a value obtained by measuring a polynucleotide selected from the polynucleotides described in Section 2 above, or a fragment thereof. Specifically, the explanatory variable of the present invention for discriminating a prostate cancer patient from a subject without prostate cancer is a gene expression level selected from, for example, the following (1) and (2):

(1) the gene expression level in sera of a prostate cancer patient and a subject without prostate cancer as measured by any DNA comprising 15 or more consecutive nucleotides in the nucleotide sequence shown in any of SEQ ID NOs: 1 to 4 or in a complementary sequence thereof; and (2) the gene expression level in sera of a prostate cancer patient and a subject without prostate cancer as measured by any DNA comprising 15 or more consecutive nucleotides in the nucleotide sequence shown in any of SEQ ID NOs: 5 to 8 or in a complementary sequence thereof.

As described above, the method for determining or evaluating whether or not a subject has prostate cancer using a sample from the subject necessitates the use of a discriminant formula employing one or more gene expression levels as an explanatory variable. In order to improve the accuracy of the discriminant formula employing only a single gene expression level, in particular, it is necessary to use a gene exhibiting a clear difference in expression levels between two groups consisting of a group of prostate cancer patients and a group of subjects without prostate cancer, in a discriminant formula.

Specifically, the gene that is used for an explanatory variable of a discriminant formula is preferably determined as follows. First, comprehensive gene expression levels of a group of prostate cancer patients and comprehensive gene expression levels of a group of test subjects without prostate cancer, both of which are in a training cohort, are used as a data set, and the degree of difference in the expression level of each gene between the two groups is obtained with the use of, for example, the P value of a parametric analysis such as the t-test, the P value of a nonparametric analysis such as the Mann-Whitney's U test, or the P value of the Wilcoxon test.

The gene can be regarded as being statistically significant when the critical rate (significance level) as the P value obtained by the test is smaller than, for example, 5%, 1%, or 0.01%.

In order to correct an increased probability of type I error attributable to the repetition of test, a method known in the art, such as the Bonferroni or Holm method, can be used for the correction (e.g., Yasushi Nagata et al., "Basics of statistical multiple comparison methods," Scientist Press Co., Ltd. (Tokyo, Japan) (2007)). In the case of the Bonferroni correction, for example, the P value obtained by a test is multiplied by the number of repetitions of test, i.e., the number of genes used in the analysis, and the obtained value is compared with a desired significance level, so that a possibility of type I error caused in the entire tests can be suppressed.

Instead of the test, the absolute value (fold change) of an expression ratio of a median value of each gene expression level between gene expression levels of a group of prostate cancer patients and gene expression levels of a group of test subjects without prostate cancer may be calculated to select a gene that is used for an explanatory variable in a discriminant formula. Alternatively, ROC curves may be prepared using gene expression levels of a group of prostate cancer patients and a group of test subjects without prostate cancer, and a gene that is used for an explanatory variable in a discriminant formula can be selected on the basis of an AUROC value.

Next, a discriminant formula that can be calculated by various methods described above is prepared using any number of genes exhibiting a large difference in their gene expression levels determined here. Examples of the method for constructing a discriminant that produces the largest discrimination accuracy include a method of constructing a discriminant formula in every combination of genes that satisfy the significance level being P value, and a method of repetitively evaluating the genes for use in the preparation of a discriminant formula while increasing the number of genes one by one in descending order of difference in gene expression level (Furey T S. et al., 2000, Bioinformatics., Vol. 16, pp. 906-14). To the discriminant formula, the gene expression level of another independent prostate cancer patient or a test subject without prostate cancer is assigned as an explanatory variable to calculate discrimination results of the group to which the independent prostate cancer patient or the test subject without prostate cancer belongs. Specifically, the set of genes for diagnosis found and the discriminant formula constructed using the set of genes for diagnosis can be evaluated in an independent sample cohort to find more universal set of genes for diagnosis that can detect prostate cancer and a more universal method for discriminating prostate cancer.

When preparing a discriminant formula using expression levels of a plurality of genes as explanatory variables, it is not necessary to select a gene exhibiting a clear difference in expression levels between the group of prostate cancer patients and the group of test subjects without prostate cancer as described above. Even if there is no clear difference in expression levels of individual genes, specifically, a discriminant formula with high discriminant performance may be obtained with the use of expression levels of a plurality of genes in combination. Thus, a method of directly searching for a discriminant formula with high discriminant performance can be employed without selecting the gene to be employed in the discriminant formula in advance.

The split-sample method is preferably used for evaluating the performance (generality) of the discriminant formula. Specifically, a data set is divided into a training cohort and a validation cohort, and gene selection by a statistical test and preparation of a discriminant formula are performed in the training cohort. Accuracy, sensitivity, and specificity are calculated using the results of discrimination of a validation cohort according to the discriminant formula and a true group to which the validation cohort belongs, to thereby evaluate the performance of the discriminant. On the other hand, gene selection by a statistical test and preparation of a discriminant formula may be performed using all the samples without dividing a data set, and accuracy, sensitivity, and specificity can be calculated according to the discriminant formula using a newly prepared sample cohort for evaluation of the performance of the discriminant.

The present invention provides a polynucleotide for detection or diagnosis of a disease that is useful for diagnosis and treatment of prostate cancer, a method for detecting prostate cancer using the polynucleotide, and a kit and a device for detecting prostate cancer comprising the polynucleotide. According to conventional diagnosis, in particular, a subject without prostate cancer may be misdiagnosed as a prostate cancer patient, which leads to needless additional testing, or opportunities for treatment may be lost because of a failure to detect prostate cancer. According to the present invention, in contrast, prostate cancer can be accurately identified in a non-invasive manner with a small amount of a sample, irrespective of the stage, the degree of infiltration, the histological grade, and the primary or recurrent phase. Specifically, the present invention provides a kit or device for diagnosis of a disease useful for diagnosis and treatment of prostate cancer with the use of highly accurate prostate cancer markers, and a method for determining (or detecting) prostate cancer.

A set of genes for diagnosis may comprise any combination selected from among, for example, one, two, or more of the above polynucleotides comprising a nucleotide sequence shown in any of SEQ ID NOs: 1 to 4 or a complementary sequence thereof, and, according to need, one, two, or more of the above polynucleotides comprising a nucleotide sequence shown in any of SEQ ID NOs: 5 to 8 or a complementary sequence thereof. In addition, a discriminant formula is constructed using the expression levels of the set of genes for diagnosis in samples from patients diagnosed to have prostate cancer as a result of tissue diagnosis and samples from subjects without prostate cancer. As a result, whether or not a subject, from which an unknown sample is provided, has prostate cancer can be determined with 96% accuracy at the highest by measuring expression levels of the set of genes for diagnosis in the unknown sample.

The kit and the method, etc. according to the present invention enable detection of prostate cancer with high sensitivity, which leads to early detection of prostate cancer. As a result, early treatment becomes possible, and viability can be improved to a significant extent. In addition, it becomes possible to avoid loss of treatment opportunities caused by a failure to detect prostate cancer or needless additional testing performed based on misdiagnosis of a subject without prostate cancer as a prostate cancer, which are necessitated due to high fluctuation observed among persons involved in urine cytology or different results attained because of subjective views of operators of prostate endoscopy.

EXAMPLES

The present invention is described in greater detail with reference to the following examples, although the technical scope of the present invention is not limited to these examples.

Reference Example

<Collection of Samples>

The informed consents were obtained from 1,044 prostate cancer patients who were diagnosed with prostate cancer as a result of prostate needle biopsy, 241 patients with benign prostatic diseases who were suspected of prostate cancer but diagnosed without prostate cancer as a result of prostate needle biopsy, and 41 healthy male subjects without cancer history and a history of hospitalization during the foregoing 3 months, and serum samples were obtained therefrom using Venoject II evacuated blood-sampling tubes (VP-AS109K63, Terumo Corporation, Japan). Among these subjects, 41 subjects were excluded from the targets because of a lack of clinical information, 3 subjects were excluded because of the incidence of other cancers, 181 subjects were excluded because of the influence of treatment prior to blood sampling, and 13 subjects were excluded because of the insufficient quality in the gene expression level measurement described below. That is, serum samples collected from 809 prostate cancer patients, 241 patients with benign prostatic diseases, and 41 healthy subjects were used.

The age distribution of these cases was as follows: prostate cancer patients: 67-year-old on average (62-year-old at the youngest to 73-year-old at the oldest); patients with benign prostatic diseases: 66-year-old on average (61-year-old at the youngest to 70-year-old at the oldest); and healthy subjects: 70-year-old on average (48-year-old at the youngest to 77-year-old at the oldest).

The distribution of the Gleason scores indicating the grade of cancer malignancy in prostate cancer cases was as follows: the number of cases with the Gleason score of 6: 86; the number of cases with the Gleason score of 3+4: 244; the number of cases with the Gleason score of 4+3: 159; and the number of cases with the Gleason score of 8 or greater: 320.

The distribution of T classification indicating a tumor size in prostate cancer cases was as follows: 256 patients had T1c; 354 patients had T2a to T2c; 183 patients had T3a to T3b; and 16 patients had T4.

The distribution of N classification indicating the presence or absence of lymph node metastasis in prostate cancer cases was as follows: 54 patients with lymph node metastasis (N1); and 755 patients without lymph node metastasis (N0).

The distribution of M classification indicating the presence or absence of distant metastasis in prostate cancer cases was as follows: 64 patients with distant metastasis (M1); and 745 patients without distant metastasis (M0). The aforementioned clinical information is collectively shown in Table 2.

TABLE 2

| Prostate cancer | Total number of cases | 809 |
| --- | --- | --- |
| | Average age (youngest to oldest) | 67 (62-73) |
| | Gleason grading system | |
| | 6 | 86 |
| | 3 + 4 | 244 |
| | 4 + 3 | 159 |
| | ≥8 | 320 |
| | T classification | |
| | T1c | 256 |
| | T2a-c | 354 |
| | T3a-b | 183 |
| | T4 | 16 |
| | N classification | |
| | N1 | 54 |
| | N0 | 755 |
| | M classification | |
| | M1 | 64 |
| | M0 | 745 |
| Benign prostatic disease | Total number of cases | 241 |
| | Average age (youngest to oldest) | 66 (61-70) |
| Healthy males | Total number of cases | 41 |
| | Average age (youngest to oldest) | 70 (48-77) |

<Extraction of Total RNA>

Total RNA was obtained using a reagent for RNA extraction in 3D-Gene (registered trademark) RNA extraction reagent from liquid sample kit (Toray Industries, Inc., Japan) according to the protocol provided by the manufacturer from 300 µl each of the serum samples obtained from the 1,091 subjects in total.

<Measurement of Gene Expression Level> miRNA in the total RNA, which was obtained from the serum samples of the 1,091 subjects, was fluorescence-labeled with the use of 3D-Gene (registered trademark) miRNA Labeling kit (Toray Industries, Inc.) according to the protocol provided by the manufacturer. The oligo DNA chip used was 3D-Gene (registered trademark) Human miRNA Oligo chip (Toray Industries, Inc.) with attached probes having sequences complementary to 2,588 miRNAs among the miRNAs registered in miRBase Release 21. Hybridization was carried out under stringent conditions, followed by washing, in accordance with the protocol provided by the manufacturer. The DNA chip was scanned using 3D-Gene (registered trademark) scanner (Toray Industries, Inc.) to obtain images. Fluorescence intensity was digitized using 3D-Gene (registered trademark) Extraction (Toray Industries, Inc.).

The digitized fluorescence intensity was used to calculate the expression level of the genes detected in the manner described below. At the outset, the highest 5% and the lowest 5% of signal intensities at a plurality of negative control spots were excluded, the value; mean+2×standard error, thereof was calculated, and genes exhibiting signal intensities higher than the calculated value were regarded as being detected. From the signal intensity of the detected gene, the average signal intensity at the negative control spots from which the highest 5% and the lowest 5% of signal intensities had been excluded was subtracted, the calculated value was converted to a logarithmic value having a base of 2 and used as a gene expression level. For data normalization, the average of 3 types of miRNAs that are reported as endogenous controls: miR-149-3p, miR-2861, and miR-4463 (Shimomura et al., Cancer Science, 2016, Vol. 107, pp. 326-34), were used to normalize the data of different samples. The normalized data of the genes that were not detected above were converted to a logarithmic value 00.1 having a base of 2. Thus, signal intensities indicating the comprehensive gene expression levels of the miRNAs in the serum samples obtained from the 1,091 subjects described above were obtained.

A method of identifying prostate cancer was constructed step by step as described below. Specifically, all the cases were first divided into 3 groups of a search cohort, a training cohort, and a validation cohort, the search cohort was subjected to candidate marker extraction, the training cohort was subjected to construction of a discriminant formula, and the validation cohort was subjected to validation of the constructed discriminant formula. A total of 123 cases: 41 cases each of prostate cancer patients, patients with benign prostatic diseases, and healthy subjects, were classified into the search cohort, a half of the remaining cases was classified into the training cohort, and another half of the remaining cases was classified into the validation cohort (i.e., a total of 484 cases: 384 prostate cancer patients and 100 patients with benign prostatic diseases). These cases were classified, so as to adjust the conditions, such as the age distribution, the Gleason grading system, T classification, N classification, and M classification, equivalent among the groups.

Calculation and statistical analysis using the digitized gene expression levels of the miRNAs were carried out using R language 3.3.1 (R Core Team, 2016, R: A language and environment for statistical computing, R Foundation for Statistical Computing, Vienna, Austria. URL https://www.R-project.org/.) and MASS package 7.3.45 (Venables, W. N. & Ripley, B. D., 2002, Modern Applied Statistics with S., Fourth Edition. Springer, New York, ISBN 0-387-95457-0).

Example 1

<Analysis of Identification of Prostate Cancer Using Discriminant Formula Using a Single Type of miRNA>

In this example, a type of miRNA extracted as a candidate marker in the search cohort was used to prepare a discriminant formula in the training cohort, and performance of the prepared discriminant formula was examined in the validation cohort.

Figure 2:
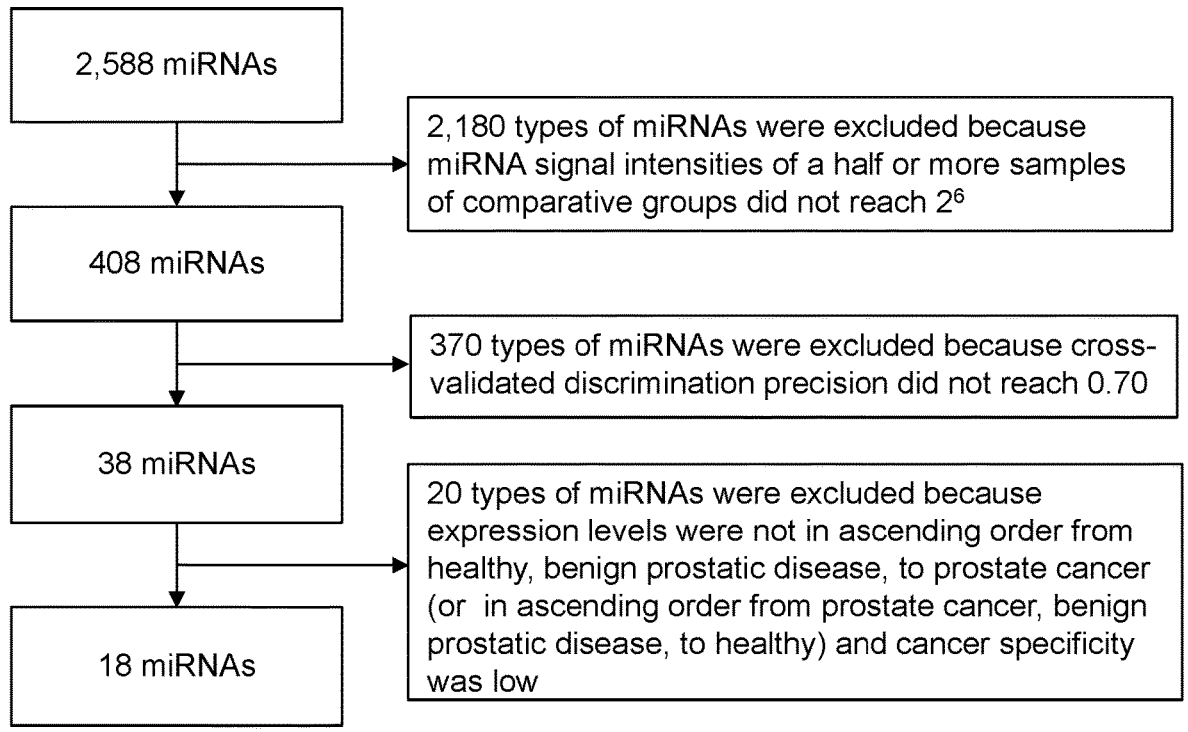
FIG. 2 schematically shows a process of selecting candidate prostate cancer markers selected from among 2,588 types of human blood microRNAs.

In order to acquire more reliable diagnostic markers from among a total of 2,588 types of miRNAs existing in humans (analytes), specifically, the number of candidate markers was first reduced in the search cohort in accordance with the scheme shown in FIG. 2. The 2,180 types of miRNAs without a gene expression level of $2^6$ or larger in 50% or more of the samples in either the positive sample group (prostate cancer patients) or the negative sample group (patients with benign prostatic disease and healthy subjects) were excluded because of low signal intensity and a lack of reliability, and remaining 408 types of miRNAs were subjected to the subsequence procedure. The cross validation was then performed, 370 types of miRNAs with the accuracy of less than 0.7 were excluded, the 38 types of miRNAs remaining in the end were analyzed to exclude 20 types of miRNAs with the average expression level that does not satisfy the correlation: healthy subjects <patients with benign prostatic diseases <prostate cancer patients, or the correlation: prostate cancer patients <patients with benign prostatic diseases <healthy subjects, because of low cancer specificity. The 18 types of miRNAs remaining in the end were identified as candidate markers.

Next, Fisher's discriminant analysis was performed on the measured expression levels of the 18 types of miRNAs in the training cohort, and cross validation was also performed to construct discriminant formulae to determine the presence or absence of prostate cancer.

Figure 3:
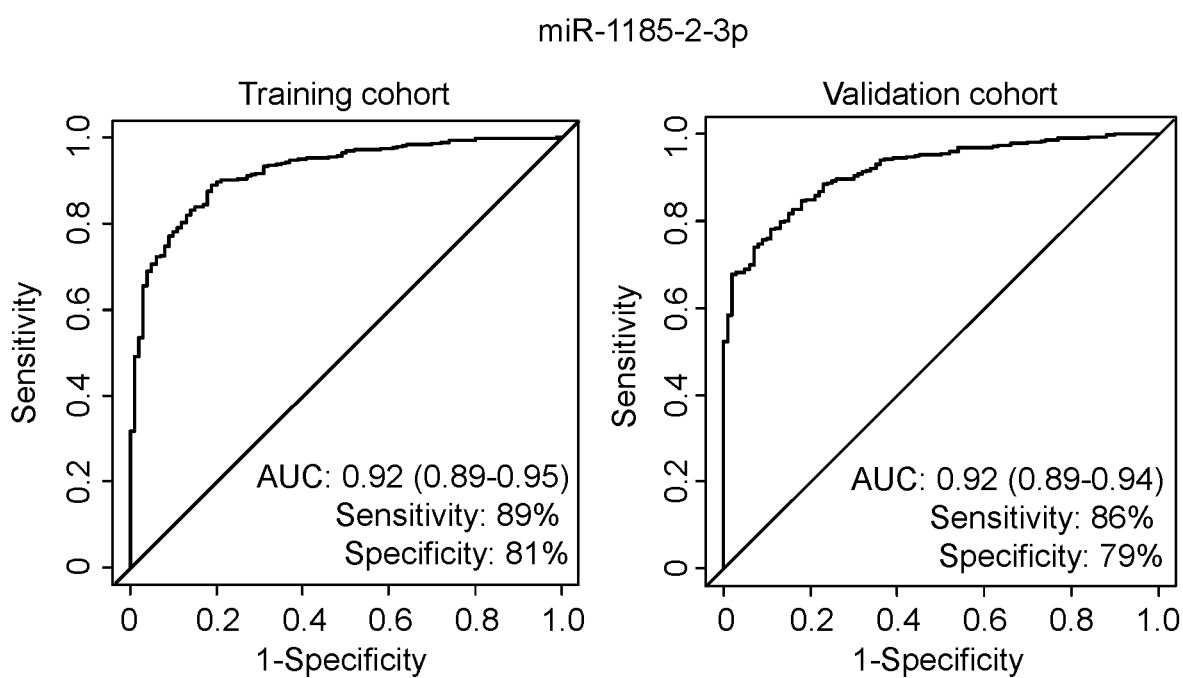
FIG. 3 shows a receiver operating characteristic (ROC) curve when prostate cancer is identified using miR-1185-2-3p of a training cohort and of a validation cohort and sensitivity and specificity at the maximal area under the curve (AUC) under the ROC curve.

As a result, the discriminant capability of 8 types of polynucleotides consisting of the nucleotide sequences shown in SEQ ID NOs: 1 to 8 examined in the training cohort was also examined in the validation cohort. For example, AUC of a polynucleotide consisting of the nucleotide sequence shown in SEQ ID NO: 1 was 0.921 in the training cohort, and it was 0.917 in the validation cohort (FIG. 3). Also, AUCs of polynucleotides consisting of the nucleotide sequences shown in SEQ ID NOs: 2 to 8 were 0.921, 0.568, 0.936, 0.971, 0.836, 0.843, and 0.707, respectively, in the training cohort, and such values were 0.913, 0.607, 0.940, 0.913, 0.815, 0.822, and 0.733, respectively, in the validation cohort (Table 3).

TABLE 3

| SEQ ID NO: | miRNA marker | AUC | |
|---|---|---|---|
| | | Training cohort | Validation cohort |
| 1 | hsa-miR-1185-2-3p | 0.921 | 0.917 |
| 2 | hsa-miR-1185-1-3p | 0.921 | 0.913 |
| 3 | hsa-miR-197-5p | 0.568 | 0.607 |

TABLE 3-continued

| SEQ ID NO: | miRNA marker | AUC | |
|---|---|---|---|
| | | Training cohort | Validation cohort |
| 4 | hsa-miR-6076 | 0.936 | 0.940 |
| 5 | hsa-miR-17-3p | 0.971 | 0.913 |
| 6 | hsa-miR-320b | 0.836 | 0.815 |
| 7 | hsa-miR-6819-5p | 0.843 | 0.822 |
| 8 | hsa-miR-1228-5p | 0.707 | 0.733 |

Figure 4:
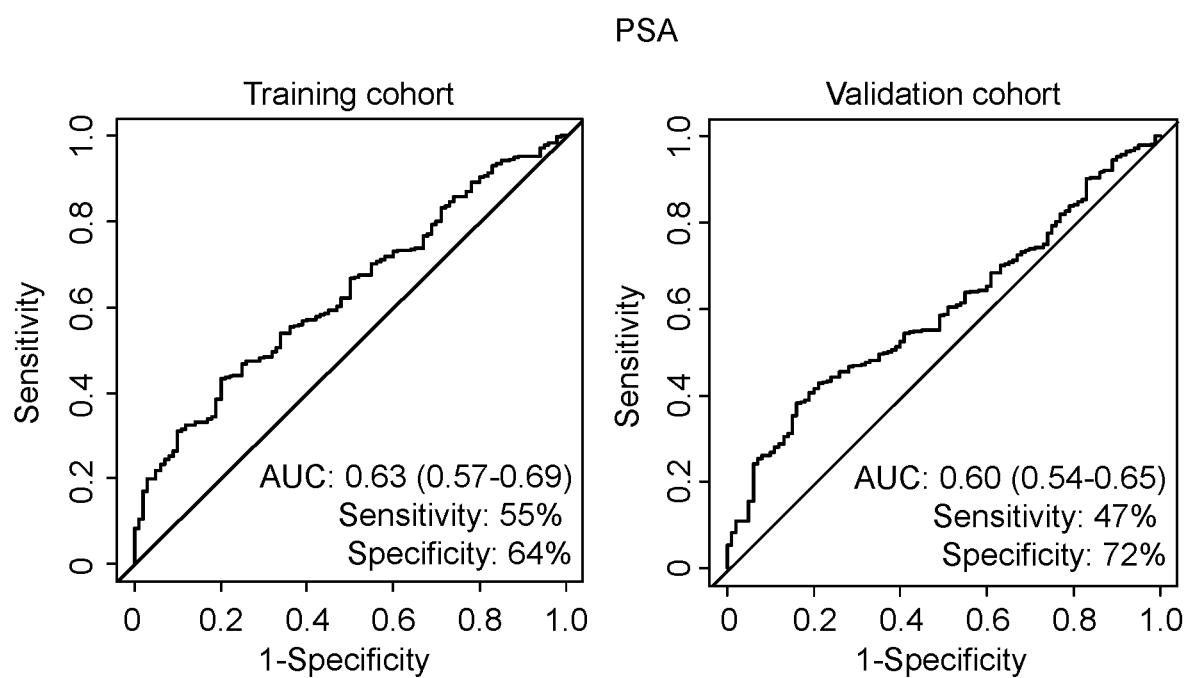
FIG. 4 shows a receiver operating characteristic (ROC) curve when prostate cancer is identified using PSA of a training cohort and of a validation cohort and sensitivity and specificity at the maximal area under the curve (AUC) under the ROC curve.

AUC of PSA that is a conventional prostate cancer marker measured in the same sample group was 0.63 in the training cohort and 0.60 in the validation cohort (FIG. 4).

Specifically, each of the 7 types of polynucleotides consisting of the nucleotide sequences shown in SEQ ID NOs: 1, 2, 4, 5, 6, 7, and 8 was capable of identifying prostate cancer by itself with a discrimination capability superior to that of PSA.

In addition, a discriminant formula was identified by designating a specific discriminant threshold, and the markers were evaluated in terms of sensitivity and specificity. When a value obtained by the discriminant formula prepared with the use of the expression level of a polynucleotide consisting of the nucleotide sequence shown in SEQ ID NO: 1 (0.903*[hsa-miR-1185-2-3p]-6.870) is a positive value, for example, the subject can be evaluated to be with prostate cancer. In the case of a negative value, the subject can be evaluated to be without prostate cancer. Table 4 shows sensitivity and specificity determined by the discriminant formulae prepared with the use of the expression levels of polynucleotides consisting of the nucleotide sequences shown in SEQ ID NOs: 1 to 8.

TABLE 4

| SEQ ID NO: | Discriminant formula | Training cohort | | Validation cohort | |
|---|---|---|---|---|---|
| | | Sensitivity | Specificity | Sensitivity | Specificity |
| 1 | 0.903*[hsa-miR-1185-2-3p] − 6.870 | 0.891 | 0.810 | 0.857 | 0.790 |
| 2 | 1.006*[hsa-miR-1185-1-3p] − 8.195 | 0.807 | 0.880 | 0.763 | 0.910 |
| 3 | 1.643*[hsa-miR-197-5p] − 14.150 | 0.497 | 0.680 | 0.523 | 0.660 |
| 4 | 1.409*[hsa-miR-6076] − 10.771 | 0.839 | 0.930 | 0.844 | 0.900 |
| 5 | 0.767*[hsa-miR-17-3p] − 3.281 | 0.883 | 0.930 | 0.870 | 0.830 |
| 6 | 0.789*[hsa-miR-320b] − 4.340 | 0.711 | 0.820 | 0.688 | 0.770 |
| 7 | 2.252*[hsa-miR-6819-5p] − 18.424 | 0.708 | 0.830 | 0.721 | 0.800 |
| 8 | −4.273*[hsa-miR-1228-5p] + 47.277 | 0.552 | 0.810 | 0.537 | 0.840 |

Of the discriminant formula employing SEQ ID NO: 1, for example, the sensitivity was 0.891 and the specificity was 0.810 in the training cohort, and the sensitivity was 0.857 and the specificity was 0.790 in the validation cohort. Of the discriminant formula employing SEQ ID NO: 2, the sensitivity was 0.807 and the specificity was 0.880 in the training cohort, and the sensitivity was 0.763 and the specificity was 0.910 in the validation cohort. Of the discriminant formula employing SEQ ID NO: 3, the sensitivity was 0.497 and the specificity was 0.680 in the training cohort, and the sensitivity was 0.523 and the specificity was 0.660 in the validation cohort. Of the discriminant formula employing SEQ ID NO: 4, the sensitivity was 0.839 and the specificity was 0.930 in the training cohort, and the sensitivity was 0.844 and the specificity was 0.900 in the validation cohort. Of the discriminant formula employing SEQ ID NO: 5, the sensitivity was 0.883 and the specificity was 0.930 in the training cohort, and the sensitivity was 0.870 and the specificity was 0.830 in the validation cohort. Of the discriminant formula employing SEQ ID NO: 6, the sensitivity was 0.711 and the specificity was 0.820 in the training cohort, and the sensitivity was 0.688 and the specificity was 0.770 in the validation cohort. Of the discriminant formula employing SEQ ID NO: 7, the sensitivity was 0.708 and the specificity was 0.830 in the training cohort, and the sensitivity was 0.721 and the specificity was 0.800 in the validation cohort. Of the discriminant formula employing SEQ ID NO: 8, the sensitivity was 0.552 and the specificity was 0.810 in the training cohort, and the sensitivity was 0.537 and the specificity was 0.840 in the validation cohort.

When a general threshold (i.e., 4 ng/ml) was used for PSA that is a conventional prostate cancer marker measured in the same sample group, the sensitivity was 0.55 and the specificity was 0.64 in the training cohort, and the sensitivity was 0.47 and the specificity was 0.72 in the validation cohort.

Specifically, each of the 7 types of polynucleotides consisting of the nucleotide sequences shown in SEQ ID NOs: 1, 2, 4, 5, 6, 7, and 8 enabled discrimination of a prostate cancer patient from a patient with a benign disease who was suspected of prostate cancer with sensitivity and specificity superior to those of PSA.

Example 2

<Analysis of Identification of Prostate Cancer Using Discriminant Formula Using 2 or More Types of miRNAs>

In this example, the 18 types of miRNAs extracted as candidate markers in the search cohort were used in multiple combinations to prepare discriminant formulae in the training cohort, and performance of the discriminant formulae prepared in the validation cohort was examined. Specifically, the expression levels of the 18 types of miRNAs obtained in the training cohort were each subjected to the Fisher's linear discriminant analysis, and cross validation was also performed to construct discriminant formulae to determine the presence or absence of prostate cancer.

As a result, the discriminant capability of the discriminant formula using 8 types of polynucleotides consisting of the nucleotide sequences shown in SEQ ID NOs: 1 to 8 in combination examined in the training cohort was found to be improved from the discriminant capability of a polynucleotide consisting of a single nucleotide sequence shown in Example 1, and high performance thereof was also examined in the validation cohort.

Figure 5:
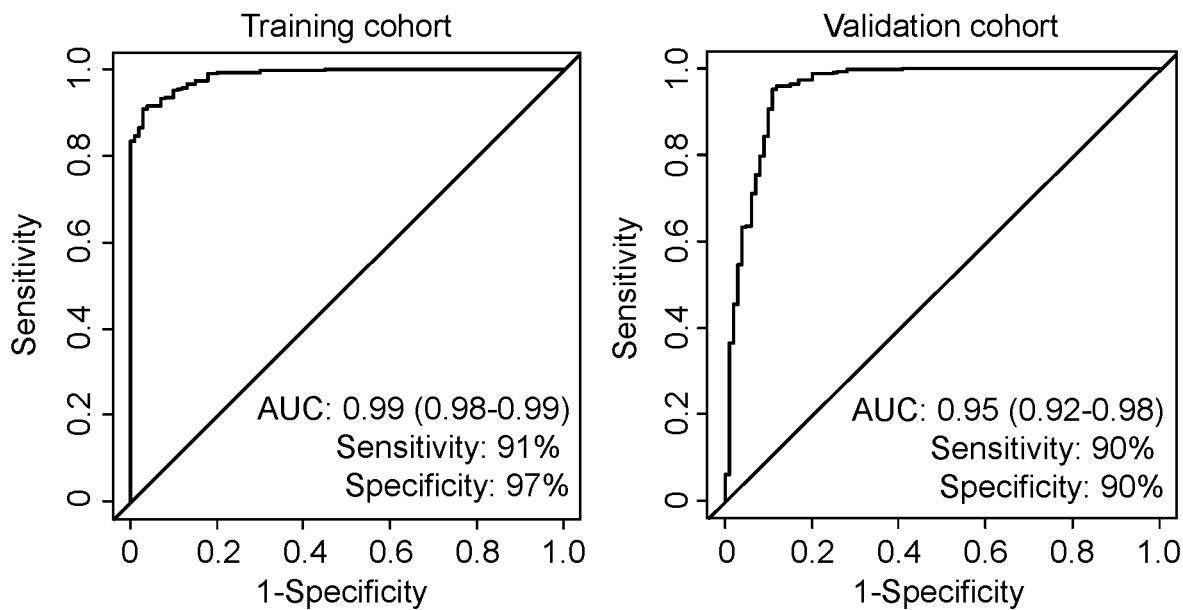
FIG. 5 shows a receiver operating characteristic (ROC) curve when prostate cancer is identified using miR-17-3p in combination with miR-1185-2-3p of a training cohort and of a validation cohort and sensitivity and specificity at the maximal area under the curve (AUC) under the ROC curve.

As described in Example 1, for example, AUC of a polynucleotide consisting of the nucleotide sequence shown in SEQ ID NO: 1 was 0.921 in the training cohort, and it was 0.917 in the validation cohort (FIG. 3). In contrast, AUC of a discriminant formula prepared with the use of polynucleotides consisting of the nucleotide sequences shown in SEQ ID NOs: 1 and 5 in combination was 0.986 in the training cohort, and it was 0.953 in the validation cohort (FIG. 5). In addition, AUC of a discriminant formula prepared with the use of, for example, polynucleotides consisting of the nucleotide sequences shown in SEQ ID NOs: 1, 3, and 5 in combination was 0.986 in the training cohort, and it was 0.953 in the validation cohort. Also, AUC of a discriminant formula prepared with the use of, for example, polynucleotides consisting of the nucleotide sequences shown in SEQ ID NOs: 2, 5, and 7 in combination was 0.985 in the training cohort, and it was 0.954 in the validation cohort. Further, AUC of a discriminant formula prepared with the use of, for example, polynucleotides consisting of the nucleotide sequences shown in SEQ ID NOs: 2, 3, 4, and 5 in combination was 0.989 in the training cohort, and it was 0.974 in the validation cohort. Further, AUC of a discriminant formula prepared with the use of, for example, polynucleotides consisting of the nucleotide sequences shown in SEQ ID NOs: 2, 3, 4, 5, and 8 in combination was 0.990 in the training cohort, and it was 0.975 in the validation cohort. Also, AUC of a discriminant formula prepared with the use of, for example, polynucleotides consisting of the nucleotide sequences shown in SEQ ID NOs: 2, 3, 4, 5, and 6 in combination was 0.990 in the training cohort, and it was 0.976 in the validation cohort.

Table 5 shows these results collectively. Such properties were also examined in the validation cohort.

TABLE 5

| Number of miRNAs subjected to discrimination | SEQ ID NO: | miRNA marker | AUC Training cohort | AUC Validation cohort |
|---|---|---|---|---|
| 1 | 1 | hsa-miR-1185-2-3p | 0.921 | 0.917 |
| 2 | 1_5 | hsa-miR-1185-2-3p, hsa-miR-17-3p | 0.986 | 0.953 |
| 3 | 1_3_5 | hsa-miR-1185-2-3p, hsa-miR-197-5p, hsa-miR-17-3p | 0.986 | 0.953 |
| 3 | 2_5_7 | hsa-miR-1185-1-3p, hsa-miR-17-3p, hsa-miR-6819-5p | 0.985 | 0.954 |
| 4 | 2_3_4_5 | hsa-miR-1185-1-3p, hsa-miR-197-5p, hsa-miR-6076, hsa-miR-17-3p | 0.989 | 0.974 |
| 5 | 2_3_4_5_8 | hsa-miR-1185-1-3p, hsa-miR-197-5p, hsa-miR-6076, hsa-miR-17-3p, hsa-miR-1228-5p | 0.990 | 0.975 |
| 5 | 2_3_4_5_6 | hsa-miR-1185-1-3p, hsa-miR-197-5p, hsa-miR-6076, hsa-miR-17-3p, hsa-miR-320b | 0.990 | 0.976 |

AUC of PSA that is a conventional prostate cancer marker measured in the same sample group was 0.63 in the training cohort and 0.60 in the validation cohort (FIG. 4).

As described above, all the discriminant formulae prepared with the use of 8 types of polynucleotides consisting of the nucleotide sequences shown in SEQ ID NOs: 1 to 8 in multiple combinations were capable of identifying prostate cancer by itself with a discrimination capability superior to that of PSA.

In addition, a discriminant formula was identified by designating a specific discriminant threshold, and the markers were evaluated in terms of sensitivity and specificity. As a result, sensitivity and specificity of the discriminant formula prepared with the use of 8 types of polynucleotides consisting of the nucleotide sequences shown in SEQ ID NOs: 1 to 8 in combination examined in the training cohort were found to be improved from those of a polynucleotide consisting of a single nucleotide sequence shown in Example 1, and high performance thereof was also examined in the validation cohort.

As described in Example 1, for example, according to the discriminant formula employing a polynucleotide consisting of the nucleotide sequence shown in SEQ ID NO: 1, the sensitivity was 0.891 and the specificity was 0.810 in the training cohort, and the sensitivity was 0.857 and the specificity was 0.790 in the validation cohort (FIG. 3). Of the discriminant formula prepared with the use of polynucleotides consisting of the nucleotide sequences shown in SEQ ID NOs: 1 and 5 in combination, in contrast, the sensitivity was 0.909 and the specificity was 0.970 in the training cohort, and the sensitivity was 0.901 and the specificity was 0.900 in the validation cohort. Of the discriminant formula prepared with the use of polynucleotides consisting of the nucleotide sequences shown in SEQ ID NO: 1, 3, and 5 in combination, the sensitivity was 0.909 and the specificity was 0.970 in the training cohort, and the sensitivity was 0.888 and the specificity was 0.900 in the validation cohort. Of the discriminant formula prepared with the use of polynucleotides consisting of the nucleotide sequences shown in SEQ ID NO: 2, 5, and 7 in combination, also, the sensitivity was 0.945 and the specificity was 0.920 in the training cohort, and the sensitivity was 0.956 and the specificity was 0.850 in the validation cohort. Of the discriminant formula prepared with the use of polynucleotides consisting of the nucleotide sequences shown in SEQ ID NO: 2, 3, 4, and 5 in combination, in addition, the sensitivity was 0.935 and the specificity was 0.950 in the training cohort, and the sensitivity was 0.927 and the specificity was 0.890 in the validation cohort. Of the discriminant formula prepared with the use of polynucleotides consisting of the nucleotide sequences shown in SEQ ID NO: 2, 3, 4, 5, and 8 in combination, in addition, the sensitivity was 0.909 and the specificity was 0.970 in the training cohort, and the sensitivity was 0.906 and the specificity was 0.900 in the validation cohort. Of the discriminant formula prepared with the use of polynucleotides consisting of the nucleotide sequences shown in SEQ ID NO: 2, 3, 4, 5, and 6 in combination, in addition, the sensitivity was 0.943 and the specificity was 0.950 in the training cohort, and the sensitivity was 0.935 and the specificity was 0.900 in the validation cohort.

Table 6 shows these results collectively. Such properties were also examined in the validation cohort.

TABLE 6

| Number of miRNAs subjected to discrimination | SEQ ID NO: | Discriminant formula | Training cohort | | Validation cohort | |
|---|---|---|---|---|---|---|
| | | | Sensitivity | Specificity | Sensitivity | Specificity |
| 1 | 1 | 0.903*[hsa-miR-1185-2-3p] − 6.870 | 0.891 | 0.810 | 0.857 | 0.790 |
| 2 | 1_5 | 0.385*[hsa-miR-1185-2-3p] + 0.657*[hsa-miR-17-3p] − 6.341 | 0.909 | 0.970 | 0.901 | 0.900 |
| 3 | 1_3_5 | 0.404*[hsa-miR-1185-2-3p] − 0.223*[hsa-miR-197-5p] + 0.660*[hsa-miR-17-3p] − 4.612 | 0.909 | 0.970 | 0.888 | 0.900 |
| 3 | 2_5_7 | 0.491*[hsa-miR-1185-1-3p] + 0.690*[hsa-miR-17-3p] − 0.439*[hsa-miR-6819-5p] − 3.708 | 0.945 | 0.920 | 0.956 | 0.850 |
| 4 | 2_3_4_5 | 0.409*[hsa-miR-1185-1-3p] − 0.408*[hsa-miR-197-5p] + 0.395*[hsa-miR-6076] + 0.583*[hsa-miR-17-3p] − 5.773 | 0.935 | 0.950 | 0.927 | 0.890 |
| 5 | 2_3_4_5_8 | 0.411*[hsa-miR-1185-1-3p] − 0.396*[hsa-miR-197-5p] + 0.382*[hsa-miR-6076] + 0.579*[hsa-miR-17-3p] − 0.156*[hsa-miR-1228-5p] − 4.176 | 0.909 | 0.970 | 0.906 | 0.900 |
| 5 | 2_3_4_5_6 | 0.404*[hsa-miR-1185-1-3p] − 0.423*[hsa-miR-197-5p] + 0.341*[hsa-miR-6076] + 0.569*[hsa-miR-17-3p] + 0.075*[hsa-miR-320b] − 5.495 | 0.943 | 0.950 | 0.935 | 0.900 |

When a general threshold (i.e., 4 ng/ml) was used for PSA that is a conventional prostate cancer marker measured in the same sample group, the sensitivity was 0.55 and the specificity was 0.64 in the training cohort, and the sensitivity was 0.47 and the specificity was 0.72 in the validation cohort.

As described above, all the discriminant formulae prepared with the use of 8 types of polynucleotides consisting of the nucleotide sequences shown in SEQ ID NOs: 1 to 8 in multiple combinations were capable of discriminating a prostate cancer patient from a patient with a benign disease who was suspected of prostate cancer with sensitivity and specificity superior to those of PSA.

Example 3

<Identification of Prostate Cancer Based on Pathological Classification by Discriminant Formula Using miRNA>

In this example, discriminant formulae of miRNAs prepared and examined in Examples 1 and 2 were used to evaluate the discrimination capability by focusing on pathological features of prostate cancer. Specifically, whether or not the discrimination capability of discriminant formulae using miRNAs would vary depending on differences in the Gleason scores indicating prostate cancer malignancy, T classification indicating a tumor size, N classification indicating the state of lymph node metastasis, and M classification indicating the state of distant metastasis was examined using the validation cohort.

Figure 6:
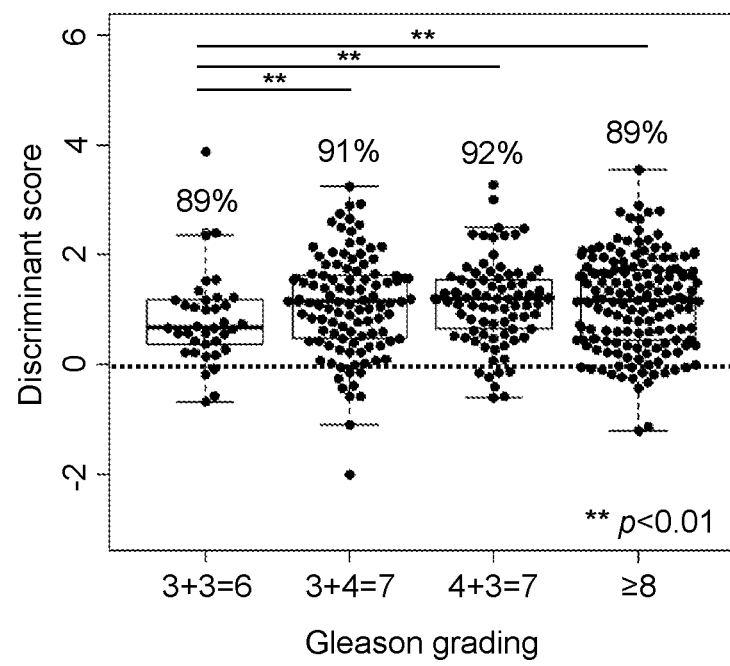
FIG. 6 shows a distribution of discriminant scores of each prostate cancer case classified by the Gleason grading system as an indicator for evaluation of prostate cancer malignancy when prostate cancer is identified using the discriminant formula prepared with miR-17-3p in combination with miR-1185-2-3p. A positive discriminant score indicates prostate cancer-positive and a negative discriminant score indicates prostate cancer-negative. A numeral value (%) of each grade indicates a proportion determined using the discriminant formula (sensitivity). A discriminant score significantly increases from the case with lower malignancy (the Gleason grading system 6) to the case with higher malignancy (the Gleason grading system 7, ≥8). In a box plot, a bold line in the middle indicates a median, a lower part of the box indicates the first quartile point, an upper part of the box indicates the third quartile point, and whiskers (error bars) each indicate a range of the minimal value and a range of the maximal value, respectively, excluding outliers.

As a result, a discriminant formula prepared with the use of, for example, polynucleotides consisting of the nucleotide sequences shown in SEQ ID NOs: 1 and 5 in combination was found to identify 89% of prostate cancer cases with the Gleason score of 3+3 (=6), 91% of prostate cancer cases with the Gleason score of 3+4 (=7), 92% of prostate cancer cases with the Gleason score of 4+3 (=7), and 89% of prostate cancer cases with the Gleason score of 8 or greater, as shown in FIG. 6. In comparison with the discriminant score with the Gleason score of 6, the discriminant score with the Gleason score of 7 or greater was increased to a significant extent (via ANOVA), which reflects prostate cancer malignancy. Specifically, the discriminant formula of interest was found to enable sufficient identification of early-stage prostate cancer with low malignancy as with the case of advanced prostate cancer.

Figure 7:
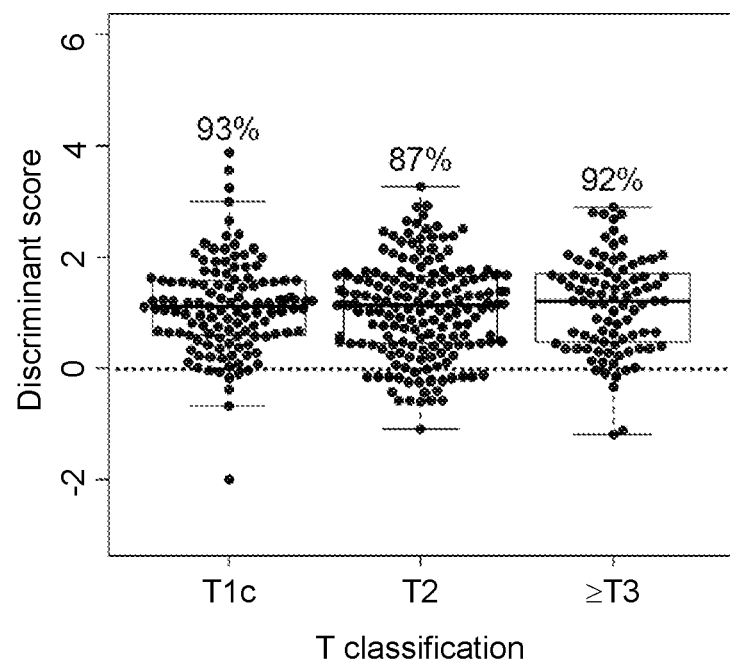
FIG. 7 shows a distribution of discriminant scores depending on prostate cancer cases divided by T classification, which is an indicator for evaluating a prostate cancer size, when prostate cancer is identified using the discriminant formula prepared with the use of miR-17-3p in combination with miR-1185-2-3p. A positive discriminant score indicates prostate cancer-positive and a negative discriminant score indicates prostate cancer-negative. A numeral value (%) of each grade indicates a proportion determined using the discriminant formula (sensitivity). In a box plot, a bold line in the middle indicates a median, a lower part of the box indicates the first quartile point, an upper part of the box indicates the third quartile point, and whiskers (error bars) each indicate a range of the minimal value and a range of the maximal value, respectively, excluding outliers.

When a discrimination capability of a discriminant formula prepared with the use of, for example, polynucleotides consisting of the nucleotide sequences shown in SEQ ID NOs: 1 and 5 in combination was evaluated in terms of T classification indicating a tumor size, as shown in FIG. 7, 93% of T1c prostate cancer cases was identified, 87% of T2 prostate cancer cases was identified, and 92% of T3 or advanced prostate cancer cases was identified. Specifically, the discriminant formula of interest was found to enable sufficient identification of early-stage prostate cancer of a small tumor size as with the case of advanced prostate cancer.

Figure 8:
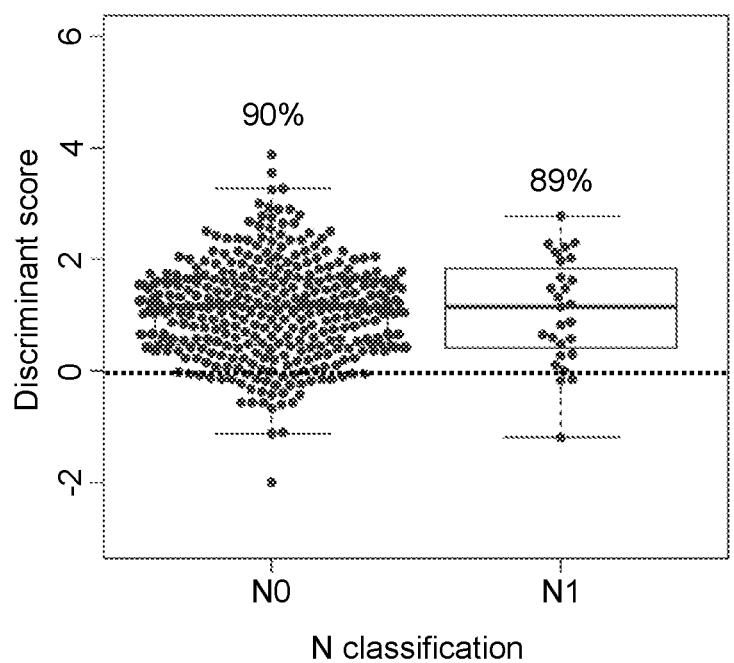
FIG. 8 shows a distribution of discriminant scores depending on prostate cancer cases divided by N classification, which is an indicator for evaluating the state of lymph node metastasis of prostate cancer, when prostate cancer is identified using the discriminant formula prepared with the use of miR-17-3p in combination with miR-1185-2-3p. A positive discriminant score indicates prostate cancer-positive and a negative discriminant score indicates prostate cancer-negative. A numeral value (%) of each grade indicates a proportion determined using the discriminant formula (sensitivity). In a box plot, a bold line in the middle indicates a median, a lower part of the box indicates the first quartile point, an upper part of the box indicates the third quartile point, and whiskers (error bars) each indicate a range of the minimal value and a range of the maximal value, respectively, excluding outliers.

When a discrimination capability of a discriminant formula prepared with the use of, for example, polynucleotides consisting of the nucleotide sequences shown in SEQ ID NOs: 1 and 5 in combination was evaluated in terms of N classification indicating a state of lymph node metastasis of cancer, as shown in FIG. 8, 90% of N0 prostate cancer cases without lymph node metastasis was identified, and 89% of N1 prostate cancer cases with lymph node metastasis was identified. Specifically, the discriminant formula of interest was found to enable sufficient identification of early-stage prostate cancer without lymph node metastasis as with the case of advanced prostate cancer.

Figure 9:
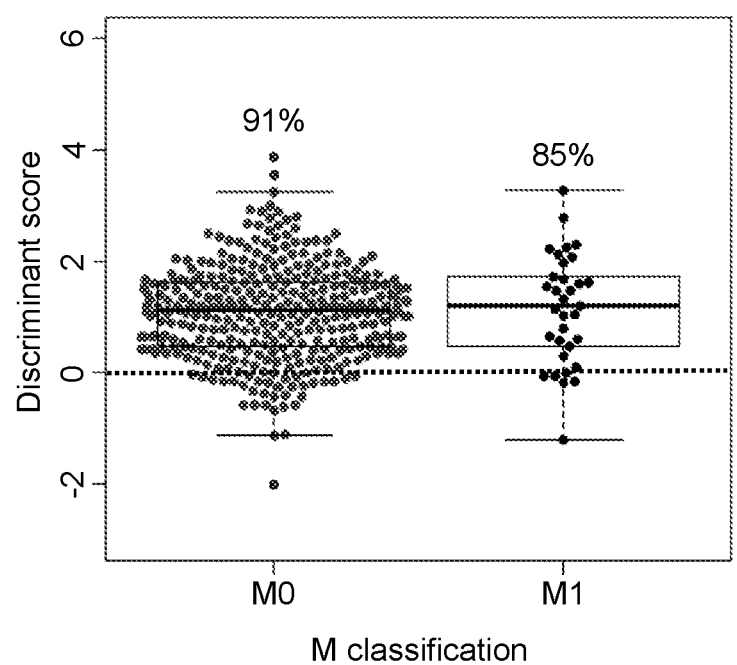
FIG. 9 shows a distribution of discriminant scores depending on prostate cancer cases divided by M classification, which is an indicator for evaluating the state of distant metastasis of prostate cancer, when prostate cancer is identified using the discriminant formula prepared with the use of miR-17-3p in combination with miR-1185-2-3p. A positive discriminant score indicates prostate cancer-positive and a negative discriminant score indicates prostate cancer-negative. A numeral value (%) of each grade indicates a proportion determined using the discriminant formula (sensitivity). In a box plot, a bold line in the middle indicates a median, a lower part of the box indicates the first quartile point, an upper part of the box indicates the third quartile point, and whiskers (error bars) each indicate a range of the minimal value and a range of the maximal value, respectively, excluding outliers.

When a discrimination capability of a discriminant formula prepared with the use of, for example, polynucleotides consisting of the nucleotide sequences shown in SEQ ID NOs: 1 and 5 in combination was evaluated in terms of M classification indicating a state of distant metastasis of cancer, as shown in FIG. 9, 91% of M0 prostate cancer cases without distant metastasis was identified, and 85% of M1 prostate cancer cases with distant metastasis was identified. Specifically, the discriminant formula of interest was found to enable sufficient identification of prostate cancer without distant metastasis at a relatively early stage as with the case of advanced prostate cancer.

The discriminant formula prepared with the use of polynucleotides consisting of the nucleotide sequences shown in SEQ ID NOs: 1 to 8 in combination as shown in Table 6 was also found to identify prostate cancer with high efficiency, regardless of the Gleason grade, T classification, N classification, or M classification.

Comparative Example 1

<Identification of Prostate Cancer Using miR-1275>

With reference to Patent Literature 1, identification of prostate cancer was attempted using miR-1275. Specifically, whether or not prostate cancer could be identified based on the miR-1275 expression levels in the serum samples used in the present invention, which were described in the reference example; i.e., serum samples obtained from 809 prostate cancer patients and 241 patients with benign prostatic diseases, was examined.

Figure 10:
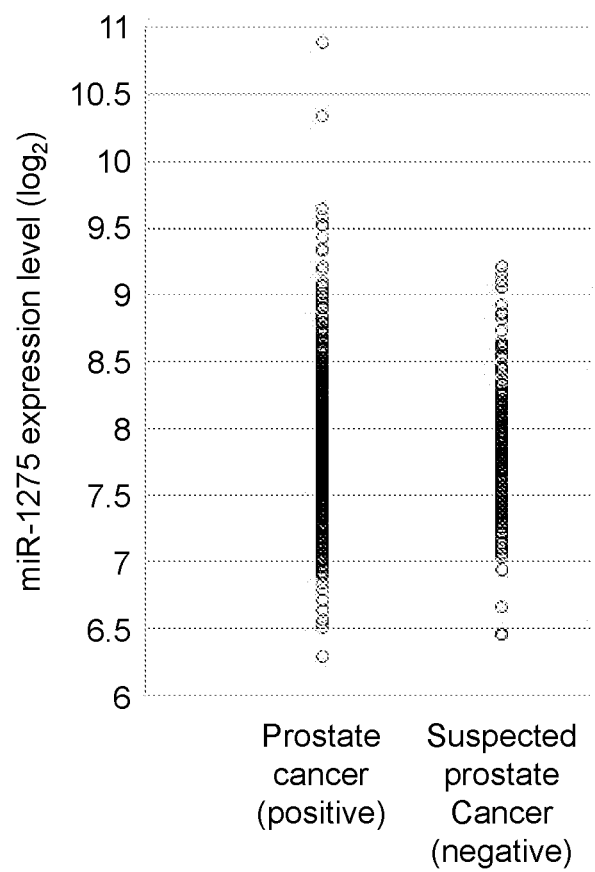
FIG. 10 shows a scatter plot indicating the miR-1275 expression levels of prostate cancer (positive) samples and suspected prostate cancer (negative) samples. The x-axis indicates the loge-transformed miR-1275 expression levels.

As a result, the distributions of the miR-1275 expression levels were found to overlap in the majority of the both sample groups (FIG. 10). When the expression level of 7.3 was designated as a threshold, for example, sensitivity was 89%, and specificity was 10%. When the expression level of 7.5 was designated as a threshold, sensitivity was 81%, and specificity was 23%. When the expression level of 7.8 was designated as a threshold, sensitivity was 55%, and specificity was 47%. Such performance cannot be sufficient for identification of prostate cancer. That is, the miR-1275 expression level cannot be employed for clinical testing.

INDUSTRIAL APPLICABILITY

According to the present invention, prostate cancer of various stages and degrees of malignancy can be effectively detected in a simple and cost-effective manner. This enables detection, diagnosis, and treatment of prostate cancer at an early stage. According to the method of the present invention, in addition, prostate cancer can be detected in a low-invasive manner with the use of the blood collected from a patient. This enables detection of prostate cancer in a simple and rapid manner.

All the publications, patents, and patent applications cited herein are incorporated herein by reference.

The invention claimed is:

1. A method for detecting prostate cancer and then treating or performing a diagnostic procedure in a human subject, comprising:
- measuring an expression level of hsa-miR-1185-2-3p in a blood, serum, or plasma sample from the subject;
- comparing the measured expression level of hsa-miR-1185-2-3p to a control expression level in a sample from a healthy subject; and
- detecting an increased level of hsa-miR-1185-2-3p in the sample from the subject as compared to the control expression level from the sample from the healthy subject;
- wherein the increased level of hsa-miR-1185-2-3p indicates that the subject has prostate cancer;
- and further treating the subject for the prostate cancer or performing a diagnostic procedure on the subject with the prostate cancer;
- wherein the treating comprises surgery, radiotherapy, chemotherapy or a combination thereof; and
- wherein the diagnostic procedure comprises rectal examination, transrectal ultrasonography of the prostate, or imaging of prostate tissue.

2. The method according to claim 1 comprising: plugging the gene expression level of hsa-miR-1185-2-3p in the sample from the subject into a discriminant formula capable of discriminating the presence or absence of prostate cancer distinctively, wherein the discriminant formula is created using gene expression levels in samples from subjects known to have prostate cancer and gene expression levels in samples from subjects having no prostate cancer as training samples; and thereby evaluating as to the presence or absence of prostate cancer in vitro.

3. The method according to claim 1, wherein the expression level of hsa-miR-1185-2-3p in the sample is measured by using a kit comprising a nucleic acid(s) that specifically binds to hsa-miR-1185-2-3p.

4. The method according to claim 3, wherein the kit further comprises at least one nucleic acid capable of specifically binding to at least one polynucleotide selected from the following other prostate cancer markers: miR-197-5p, miR-6076, and/or miR-17-3p, miR-320b, miR-6819-5p, and miR-1228-5p.

5. The method according to claim 1, wherein the expression level of hsa-miR-1185-2-3p in the sample is measured by using a device comprising a nucleic acid(s) that specifically binds to hsa-miR-1185-2-3p.

6. The method according to claim 5, wherein the device further comprises at least one nucleic acid capable of specifically binding to at least one polynucleotide selected from the following other prostate cancer markers: miR-197-5p, miR-6076, and/or miR-17-3p, miR-320b, miR-6819-5p, and miR-1228-5p.

* * * * *